United States Patent
Young et al.

(10) Patent No.: US 10,595,515 B2
(45) Date of Patent: Mar. 24, 2020

(54) ANIMAL MODELS, CELL LINES AND METHODS FOR SCREENING HEPATITIS C VIRUS VACCINES

(71) Applicant: NATIONAL RESEARCH COUNCIL OF CANADA, Ottawa (CA)

(72) Inventors: Kevin Young, Ottawa (CA); Lakshmi Krishnan, Ottawa (CA)

(73) Assignee: NATIONAL RESEARCH COUNCIL OF CANADA, Ottawa (CA)

( * ) Notice: Subject to any disclaimer, the term of this patent is extended or adjusted under 35 U.S.C. 154(b) by 0 days.

(21) Appl. No.: 15/514,806

(22) PCT Filed: Oct. 1, 2015

(86) PCT No.: PCT/CA2015/050989
§ 371 (c)(1),
(2) Date: Mar. 27, 2017

(87) PCT Pub. No.: WO2016/049769
PCT Pub. Date: Apr. 7, 2016

(65) Prior Publication Data
US 2017/0215393 A1    Aug. 3, 2017

Related U.S. Application Data

(60) Provisional application No. 62/058,533, filed on Oct. 1, 2014.

(51) Int. Cl.
| | |
|---|---|
| *C12N 5/02* | (2006.01) |
| *C12N 5/00* | (2006.01) |
| *A01K 67/027* | (2006.01) |
| *C12N 15/85* | (2006.01) |
| *A61K 39/12* | (2006.01) |
| *C12N 5/09* | (2010.01) |
| *C12N 7/00* | (2006.01) |
| *C12N 15/86* | (2006.01) |
| *C12Q 1/70* | (2006.01) |
| *A61K 39/00* | (2006.01) |

(52) U.S. Cl.
CPC .......... *A01K 67/0271* (2013.01); *A61K 39/12* (2013.01); *C12N 5/0693* (2013.01); *C12N 7/00* (2013.01); *C12N 15/85* (2013.01); *C12N 15/86* (2013.01); *A01K 2207/12* (2013.01); *A01K 2227/105* (2013.01); *A01K 2267/0331* (2013.01); *A01K 2267/0337* (2013.01); *A01K 2267/0393* (2013.01); *A61K 2039/523* (2013.01); *A61K 2039/5256* (2013.01); *C12N 2710/10343* (2013.01); *C12N 2770/24222* (2013.01); *C12N 2770/24234* (2013.01); *C12N 2840/206* (2013.01); *C12Q 1/707* (2013.01)

(58) Field of Classification Search
CPC .................................................... A61K 39/12
See application file for complete search history.

(56) References Cited

U.S. PATENT DOCUMENTS

| | | | |
|---|---|---|---|
| 6,127,116 | A | 10/2000 | Rice et al. |
| 7,416,840 | B2 | 8/2008 | Zhu et al. |
| 2006/0004976 | A1 | 3/2006 | Min |
| 2009/0214593 | A1 | 8/2009 | Sallberg et al. |

FOREIGN PATENT DOCUMENTS

| | | |
|---|---|---|
| WO | 2002/038793 A2 | 5/2002 |
| WO | 2005/053516 A2 | 6/2005 |
| WO | 2007/011777 A2 | 1/2007 |
| WO | 2009/005615 A1 | 1/2009 |

OTHER PUBLICATIONS

Ahlen et al., "Methods for Monitoring Gene Gun-Induced HBV- and HCV-Specific Immune Responses in Mouse Models", In: Sudowe S., Reske-Kunz A. (eds) Biolistic DNA Delivery. Methods in Molecular Biology (Methods and Protocols), vol. 940. Humana Press, Totowa, NJ, 2013, pp. 239-267.
Arterburn, L. M., et al., "A morphological study of differentiated hepatocytes in vitro. Hepatology", Jul. 1995;22(1):175-187.
Dong, X.M., "HCV-Core Over-expressed Specifically in Liver Cells", Thesis. University of Ottawa, 2007.
Dorner, M., et al., "Completion of the entire hepatitis C virus life-cycle in genetically humanized mice", Nature, Sep. 2013;501(7466):237-241.
Frahm, M., et al., "Efficiency of Conditionally Attenuated *Salmonella enterica* Serovar Typhimurium in Bacterium-Mediated Tumor Therapy", mBio, 2015;6(2):1-11.
Frentzen, et al., "Cell Entry, efficient RNA replication, and production of infectious hepatitis C virus progeny in mouse liver-derived cells", Hepatology, 2014;59(1):78-88.
Fytili, P., et al., "Cross-genotype-reactivity of the immunodominant HCV CD8 T-cell epitope NS3-1073", Vaccine, 2008;26:3818-3826.
Gilbert, R., et al., "Establishment and validation of new complementing cells for production of E1-deleted adenovirus vectors in serum-free suspension culture", J Virol Methods, Nov. 2014;208:177-188.
Gower, E., et al., "Global epidemiology and genotype distribution of the hepatitis C virus infection", J Hepatol., Nov. 2014;61(1 Suppl): S45-57.

(Continued)

*Primary Examiner* — Valarie E Bertoglio
(74) *Attorney, Agent, or Firm* — Gavrilovich, Dodd & Lindsey LLP

(57) ABSTRACT

Modified non-human mammalian hepatoma cell lines that express hepatitis C virus (HCV) antigens and which are capable of generating tumours in a syngeneic animal model are provided. The cell lines are generated by genomic integration of an expression construct that comprises one or more HCV antigen-encoding sequences under the control of a constitutive promoter. The expression construct further comprises a selectable marker and a reporter gene under the control of the same promoter. The cell lines are useful for testing prophylactic and therapeutic vaccines against HCV either in vitro or in vivo.

12 Claims, 10 Drawing Sheets

Specification includes a Sequence Listing.

(56) References Cited

OTHER PUBLICATIONS

Harty, J. T., et al., "Specific Immunity to Listeria monocytogenes in the Absence of IFN$_\gamma$", Immunity, Jul. 1995;3:109-117.

He, T-C., et al., "A simplified system for generating recombinant adenoviruses", Proc Natl Acad Sci, Mar. 1998; 95:2509-2514.

Hiroshima, Y., et al., "Comparison of efficacy of *Salmonella typhimurium* A1-R and chemotherapy on stem-like and non-stem human pancreatic cancer cells", Cell Cycle, Aug. 6, 2013; 12(17):2774-2780.

Ip, P.P., et al., "Alphavirus-based Vaccines Encoding Nonstructural Proteins of Hepatitis C Virus Induce Robust and Protective T-cell Responses", Molecular Therapy, Apr. 2014; 22(4):881-890.

Kagi, D., et al., "CD8+ T cell-mediated protection against an intracellular bacterium by perforin-dependent cytotoxicity", Eur J Immunol., 1994;24:3068-3072.

Krishnadas, D. K., et al., "Immunomodulation by hepatitis C virus-derived proteins: targeting human dendritic cells by multiple mechanism", International Immunology, Apr. 2010;22(6):491-502.

Labonte, P., et al., "Basal Replication of Hepatitis C Virus in Nude Mice Harboring Human Tumor", J of Med Virol., 2002;66:312-319.

Lechner, F., "Analysis of successful immune responses in persons infected with hepatitis C virus," J Exp Med, May 2000;191(9):1499-1512.

Liang, T. J., and Ghany, M. G., "Current and Future Therapies for Hepatitis C Virus Infection", N Eng J Med., May 2013;368(20):1907-1917.

Long, G., et al., "Mouse Hepatic Cells support assembly of infectious Hepatitis C Virus Particles," Gastroenterology, Sep. 2011;141(3):1057-1066.

Mailly, L., et al., "Hepatitis C virus infection and related liver disease: the quest for the best animal model," Front Microbiol., Jul. 2013;4(212):1-11.

Massie, B., et al., "New adenovirus vectors for protein production and gene transfer", Cytotechnology, 1998;28:53-64.

Myers, R. P., et al., "Burden of disease and cost of chronic hepatitis C virus infection in Canada," Can J Gastroenterol Hepatol., May 2014;28(5):243-250.

Rüssmann, H., et al., "Yersinia enterocolitica-mediated translocation of defined fusion proteins to the cytosol of mammalian cells results in peptide-specific MHC class I-restricted antigen presentation," Eur J Immunol., 2000;30:1375-1384.

Satoi, J., et al., "Genetic Immunization of Wild-Type and Hepatitis C Virus Transgenic Mice Reveals a Hierarchy of Cellular Immune Response and Tolerance Induction against Hepatitis C Virus Structural Proteins", J Virol., Dec. 2001;75(24):12121-12127.

Shen, J-R., et al., "An Independent Role of Cytochrome c-550 in Cyanobacterial Photosystem II as Revealed by Double-Deletion Mutagenesis of the psbO and psbV Genes in *Synechocystis* sp. PCC 6803", Biochemistry, 1995;34(39):12661-12668.

Singh, S., et al., "Recombinant adenoviral vector expressing HCV NS4 induces protective immune responses in a mouse model of Vaccinia-HCV virus infection: A dose and route conundrum", Vaccine, 2014;32:2712-2721.

Tzelepis, F., et al., "Modulation of Antigenic Location Converts Chronic into Acute Infection by Forcing CD8+ T Cell Recognition", Cell Reports, Dec. 2012;2(6):1710-1721.

White, D. and Harty, J.T., "Perforin-Deficient CD8+ T Cells Provide Immunity to Listeria monocytogenes by a Mechanism That Is Independent of CD95 and IFN-γ but Requires TNF-α," J Immunol., Jan. 1998;160(2):898-905.

You, S., et al., "A cis-Acting Replication Element in the Sequence Encoding the NS5B RNA-Dependent RNA Polymerase is Required for Hepatitis C Virus RNA Replication," J Virol., Feb. 2004;78(3):1352-1366.

Yu, W., et al., "A novel challenge model to evaluate the efficacy of hepatitis C virus vaccines in mice," Vaccine, 2014;32:3409-3416.

Encke, J., et al., "Genetic Immunization Generates Cellular and Humoral Immune Responses Against the Nonstructural Proteins of the Hepatitis C Virus in a Murine Model", The Journal of Immunology, Nov. 1, 1998; 161(9):4917-4923.

Yuan, Z., et al., "In vivo treatment of HCV core-positive HepG2 cells with the transfer of recombinant caspase-3 using a 2'-5' OAS promoter", Molecular Medicine Reports, Dec. 9, 2011; 5(3):631-636.

Zabala, M., et al., "Evaluation of bioluminescent imaging for noninvasive monitoring of colorectal cancer progression in the liver and its response to immunogene therapy," Molecular Cancer, Jan. 2009;8:2.

A

B

C

D

SEQUENCE LISTING

<160> NUMBER OF SEQ ID NOS: 20

<210> SEQ ID NO 1
<211> LENGTH: 28
<212> TYPE: DNA
<213> ORGANISM: Artificial Sequence

```
<220> FEATURE:
<223> OTHER INFORMATION: NS3 Primer

<400> SEQUENCE: 1
ctactcccaa cagacgcgag gcctactt                                    28

<210> SEQ ID NO 2
<211> LENGTH: 28
<212> TYPE: DNA
<213> ORGANISM: Artificial Sequence
<220> FEATURE:
<223> OTHER INFORMATION: NS3 Primer

<400> SEQUENCE: 2
cgcatagtgg tttccataga ctcgacgg                                    28

<210> SEQ ID NO 3
<211> LENGTH: 20
<212> TYPE: DNA
<213> ORGANISM: Artificial Sequence
<220> FEATURE:
<223> OTHER INFORMATION: NS4b Primer

<400> SEQUENCE: 3
gcctcacacc tcccttacat                                             20

<210> SEQ ID NO 4
<211> LENGTH: 18
<212> TYPE: DNA
<213> ORGANISM: Artificial Sequence
<220> FEATURE:
<223> OTHER INFORMATION: NS4b Primer

<400> SEQUENCE: 4
gcatggcgtg gagcagtc                                               18

<210> SEQ ID NO 5
<211> LENGTH: 28
<212> TYPE: DNA
<213> ORGANISM: Artificial Sequence
<220> FEATURE:
<223> OTHER INFORMATION: NS5b Primer

<400> SEQUENCE: 5
tctacggggc ctgttactcc attgagcc                                    28

<210> SEQ ID NO 6
<211> LENGTH: 26
<212> TYPE: DNA
<213> ORGANISM: Artificial Sequence
<220> FEATURE:
<223> OTHER INFORMATION: NS5b Primer

<400> SEQUENCE: 6
ggtcgggcac gagacaggct gtgata                                      26

<210> SEQ ID NO 7
<211> LENGTH: 20
<212> TYPE: DNA
<213> ORGANISM: Artificial Sequence
<220> FEATURE:
<223> OTHER INFORMATION: B-actin Primer

<400> SEQUENCE: 7
cagccttcct tcttgggtat                                             20
```

```
<210> SEQ ID NO 8
<211> LENGTH: 20
<212> TYPE: DNA
<213> ORGANISM: Artificial Sequence
<220> FEATURE:
<223> OTHER INFORMATION: B-actin Primer

<400> SEQUENCE: 8
tggcatagag gtctttacgg                                          20

<210> SEQ ID NO 9
<211> LENGTH: 25
<212> TYPE: DNA
<213> ORGANISM: Artificial Sequence
<220> FEATURE:
<223> OTHER INFORMATION: GAPDH Primer

<400> SEQUENCE: 9
ctggtcacca gggctgccat ttgca                                    25

<210> SEQ ID NO 10
<211> LENGTH: 24
<212> TYPE: DNA
<213> ORGANISM: Artificial Sequence
<220> FEATURE:
<223> OTHER INFORMATION: GAPDH Primer

<400> SEQUENCE: 10
caccggcctc accccatttg atgt                                     24

<210> SEQ ID NO 11
<211> LENGTH: 28
<212> TYPE: DNA
<213> ORGANISM: Artificial Sequence
<220> FEATURE:
<223> OTHER INFORMATION: GFP Primer

<400> SEQUENCE: 11
gagagggtga aggtgatgca acatacgg                                 28

<210> SEQ ID NO 12
<211> LENGTH: 28
<212> TYPE: DNA
<213> ORGANISM: Artificial Sequence
<220> FEATURE:
<223> OTHER INFORMATION: GFP Primer

<400> SEQUENCE: 12
cagcacgtgt cttgtagttg ccgtcatc                                 28

<210> SEQ ID NO 13
<211> LENGTH: 24
<212> TYPE: DNA
<213> ORGANISM: Artificial Sequence
<220> FEATURE:
<223> OTHER INFORMATION: Hexon Primer

<400> SEQUENCE: 13
atggctaccc cttcgatgat gccg                                     24

<210> SEQ ID NO 14
<211> LENGTH: 25
<212> TYPE: DNA
<213> ORGANISM: Artificial Sequence
```

```
<220> FEATURE:
<223> OTHER INFORMATION: Hexon Primer

<400> SEQUENCE: 14
agggatgaac cgcagcgtca aacgc                                        25

<210> SEQ ID NO 15
<211> LENGTH: 27
<212> TYPE: DNA
<213> ORGANISM: Artificial Sequence
<220> FEATURE:
<223> OTHER INFORMATION: NS4b Primer

<400> SEQUENCE: 15
gagtcctagc agctctggcc gcgtatt                                      27

<210> SEQ ID NO 16
<211> LENGTH: 25
<212> TYPE: DNA
<213> ORGANISM: Artificial Sequence
<220> FEATURE:
<223> OTHER INFORMATION: NS4b Primer

<400> SEQUENCE: 16
atgccggcgc ctacgaaagc agaag                                        25

<210> SEQ ID NO 17
<211> LENGTH: 28
<212> TYPE: DNA
<213> ORGANISM: Artificial Sequence
<220> FEATURE:
<223> OTHER INFORMATION: NS4b Primer

<400> SEQUENCE: 17
ctgttggcag cataggcctt gggaaggt                                     28

<210> SEQ ID NO 18
<211> LENGTH: 28
<212> TYPE: DNA
<213> ORGANISM: Artificial Sequence
<220> FEATURE:
<223> OTHER INFORMATION: NS4b Primer

<400> SEQUENCE: 18
cttggactgg agccaggtct tgaaatca                                     28

<210> SEQ ID NO 19
<211> LENGTH: 25
<212> TYPE: DNA
<213> ORGANISM: Artificial Sequence
<220> FEATURE:
<223> OTHER INFORMATION: NS3 Primer

<400> SEQUENCE: 19
gcgacctgcg tcaatggcgt gtgtt                                        25

<210> SEQ ID NO 20
<211> LENGTH: 25
<212> TYPE: DNA
<213> ORGANISM: Artificial Sequence
<220> FEATURE:
<223> OTHER INFORMATION: NS3 Primer

<400> SEQUENCE: 20
tcggcatgcc tcgtgaccaa gtaaa                                        25
```

ANIMAL MODELS, CELL LINES AND METHODS FOR SCREENING HEPATITIS C VIRUS VACCINES

CROSS REFERENCE TO RELATED APPLICATION

This application is a U.S. National Stage Application filed under 35 U.S.C. § 371 and claims priority to International Application No. PCT/CA2015/050989, filed Oct. 1, 2015, which application claims priority to U.S. Provisional Application No. 62/058,533, filed Oct. 1, 2014, the disclosures of which are incorporated herein by reference in their entireties.

FIELD OF THE INVENTION

The present invention relates generally to the field of hepatitis C virus (HCV) and, in particular, to animal models and cell lines useful for testing prophylactic and therapeutic vaccines against HCV.

BACKGROUND OF THE INVENTION

Hepatitis C virus (HCV) infects 1-2% of the population world-wide, forming a chronic infection of the liver (Gower E, et al., 2014, *J Hepatol*. pii: S0168-8278(14)00526-1). Though largely asymptomatic for much of the infection, HCV-infected persons can develop cirrhosis and liver cancer during the later stages of the infection. The lack of symptoms associated with HCV infections contributes to the fact that the majority of infected persons go undiagnosed. A recent estimate in Canada has predicted that while infection rates will slowly drop over the next 20 years due to HCV screening and the use of anti-viral medications, the number of persons affected by cirrhosis and liver cancer will greatly increase, due largely to the aging of the currently infected population (Myers R P, et al., 2014, *Can J Gastroenterol Hepatol*. 28(5):243-250). New direct-acting anti-virals (DAAs) will aid in the treatment of HCV, though treatment rates will likely remain low (currently approximately 1.4% of infected persons in Canada, and approximately 5% in Britain and France), treatments are not entirely effective, and DAAs are prone to the development of resistance. The development of a therapeutic vaccine which could be used to treat large at-risk populations would help immensely to stem the oncoming tide of HCV-related disease.

Studies of HCV-infected chimpanzees and intravenous drug users have indicated that the production of a broad anti-HCV T cell response, potentially in combination with HCV neutralizing antibodies, will eliminate an HCV infection (Ghany M G, & Liang T J, 2013, *N Engl J Med*. 369(7):679-80). An estimated 20-25% of persons infected with HCV will spontaneously clear the virus, dependent on the production of a suitable immune response. Therefore, there is good reason to believe that a successful therapeutic HCV vaccine can be developed.

The largest current hurdle in the development of a successful therapeutic vaccine for HCV is the lack of animal models suitable for testing vaccine efficacy. This stems from the host-restricted nature of HCV infections, being largely restricted to infection in humans and, more specifically, human hepatocytes. Chimpanzees, though infectable, are unlikely to be used to any great extent in coming years, with the United States government no longer supporting chimpanzee use in research, and biopharmaceutical companies discontinuing their use. Vaccine efficacy testing in small animal models, generally mice, has involved the use of HCV recombinant viruses (such as vaccinia virus) (Singh S, et al., 2014, *Vaccine*. 32(23):2712-21), HCV recombinant lymphoma tumours (Ip P P, et al., 2014, *Mol Ther*. 22(4):881-90), recombinant expression of HCV antigens in the liver through transgenic modification (Satoi J, et al., 2001, *J Virol*. 75(24):12121-7), or transient expression construct delivery (Yu W, et al., 2014, *Vaccine*. 32(27):3409-16). Each of these methodologies has unique advantages and disadvantages; none mimic a chronic HCV infection very well. Recent efforts to generate a transgenic mouse that can be infected with HCV have demonstrated that HCV will only infect and persist in the livers of innate immune-incompetent mice; and even then only at very low levels (Dorner M, et al., 2013, *Nature*. 501(7466):237-41). The use of immune-incompetent animals greatly limits the use of these models in vaccine efficacy testing.

It has recently been reported that mouse cells cultured in vitro can be made to be more permissive of HCV replication (Frentzen A, et al., 2014, *Hepatology*. 59(1):78-88). This was accomplished by over-expressing the liver microRNA, miR-122, in in vitro cultured hepatoma cells that were also deficient for the anti-viral protein, MAVS. The authors suggest that such cells could potentially be used to generate clones that stably replicate HCV, and that ultimately this approach may help to develop an immune-competent small animal model for HCV.

U.S. Pat. No. 7,416,840 describes cells and cell lines which replicate HCV of non-hepatic human and non-human hepatic origin, and the use of these cells and cell lines to identify anti-HCV agents. The ability of these cells to be used to screen for anti-HCV agents is dependent on the ability of the transfected HCV sequences to self-replicate, as such, the HCV RNA used for transfection of the non-human hepatic cells had already been passaged through human non-hepatic cells and had accumulated permissive mutations allowing it to replicate in these cells.

U.S. Pat. No. 6,127,116 describes a genetically engineered HCV nucleic acid clone that is capable of replication, expression of functional HCV proteins and infection in vivo and in vitro. The nucleic acid clone includes specifically defined 3' and 5' non-translated regions (NTRs) to permit replication of the polyprotein encoding sequences within a host cell.

International Patent Application Publication No. WO 2009/005615 describes a use of the NS4B protein nucleotide binding motif (NBM) of HCV for identifying agents that inhibit a neoplastic cellular phenotype. Expression of NS4B NBM polypeptide in mammalian cells were shown to promote a neoplastic cellular phenotype, thus cells expressing NS4B NBM are described as being useful for in vitro and in vivo methods of screening for anti-cancer agents.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

The present invention relates to animal models, cell lines and methods for screening prophylactic and therapeutic HCV vaccines. In one aspect, the invention relates to a non-human mammalian hepatoma cell comprising an expression construct stably integrated into the genome of the cell, the expression construct comprising a promoter sequence operably linked to: a first nucleic acid sequence encoding one or a plurality of hepatitis C virus (HCV) proteins, and a second nucleic acid sequence encoding a selectable marker, wherein the cell constitutively expresses the one or a plurality of HCV proteins.

In another aspect, the invention relates to a non-human mammalian hepatoma cell comprising an expression construct stably integrated into the genome of the cell, the expression construct comprising a promoter sequence operably linked to: (i) a first nucleic acid sequence encoding a plurality of hepatitis C virus (HCV) proteins, (ii) a second nucleic acid sequence encoding a selectable marker, and (iii) a third nucleic acid sequence encoding a reporter, wherein the cell constitutively expresses the plurality of HCV proteins.

In another aspect, the invention relates to an in vitro method of testing a prophylactic or therapeutic hepatitis C virus (HCV) vaccine comprising: a) culturing a cell as described above to produce a cell culture; b) contacting the cell culture with serum or immune cells isolated from an animal previously treated with the HCV vaccine, and c) monitoring growth of the cell culture.

In another aspect, the invention relates to a method of producing an animal model suitable for testing prophylactic and therapeutic hepatitis C virus vaccines, the method comprising administering a cell as described above to a immunocompetent animal, and allowing the cell to proliferate and form a tumour in the mammal, wherein the cell and the immunocompetent animal are syngeneic or closely genetically related.

In another aspect, the invention relates to an animal model produced by a method as described above.

In another aspect, the invention relates to an animal model for testing prophylactic and therapeutic hepatitis C virus (HCV) vaccines, the animal bearing a tumour comprising hepatoma cells, at least one of the hepatoma cells comprising an expression construct stably integrated into the genome of the cell, the expression construct comprising a promoter sequence operably linked to: a first nucleic acid sequence encoding one or a plurality of hepatitis C virus (HCV) proteins, and a second nucleic acid sequence encoding a selectable marker, wherein the cell constitutively expresses the one or a plurality of HCV proteins, wherein the animal and the hepatoma cells are syngeneic or closely genetically related.

In another aspect, the invention relates to an animal model for testing prophylactic and therapeutic hepatitis C virus (HCV) vaccines, the animal bearing a tumour comprising hepatoma cells, at least one of the hepatoma cells comprising an expression construct stably integrated into the genome of the cell, the expression construct comprising a promoter sequence operably linked to: (i) a first nucleic acid sequence encoding a plurality of hepatitis C virus (HCV) proteins, (ii) a second nucleic acid sequence encoding a selectable marker, and (iii) a third nucleic acid sequence encoding a reporter, wherein the cell constitutively expresses the plurality of HCV proteins, wherein the animal and the hepatoma cells are syngeneic or closely genetically related.

In another aspect, the invention relates to a method of testing a prophylactic or therapeutic hepatitis C virus (HCV) vaccine comprising administering the vaccine to an animal model as described above, and assessing tumour growth.

In another aspect, the invention relates to a mammalian expression vector comprising an expression construct, the expression construct comprising: a promoter sequence operably linked to (i) a first nucleic acid sequence encoding a plurality of hepatitis C virus (HCV) proteins, (ii) a second nucleic acid sequence encoding a selectable marker, and (iii) a third nucleic acid sequence encoding a reporter protein, wherein when the vector is transfected into a mammalian cell and the cell is cultured under conditions requiring expression of the selectable marker, the vector stably integrates into the genome of the cell and the cell constitutively expresses the plurality of HCV proteins.

In another aspect, the invention relates to a method of producing a stably transfected non-human mammalian hepatoma cell capable of constitutively expressing a plurality of hepatitis C virus (HCV) proteins, the method comprising transfecting the cell with a vector as described above, and culturing the cell under conditions requiring expression of the selectable marker, wherein the expression construct stably integrates into the genome of the cell.

In another aspect, the invention relates to a kit comprising a vector as described above and instructions for use.

In another aspect, the invention relates to a kit comprising a cell as described above and instructions for use.

BRIEF DESCRIPTION OF THE DRAWINGS

These and other features of the invention will become more apparent in the following detailed description in which reference is made to the appended drawings.

DETAILED DESCRIPTION OF THE INVENTION

Figure 1:
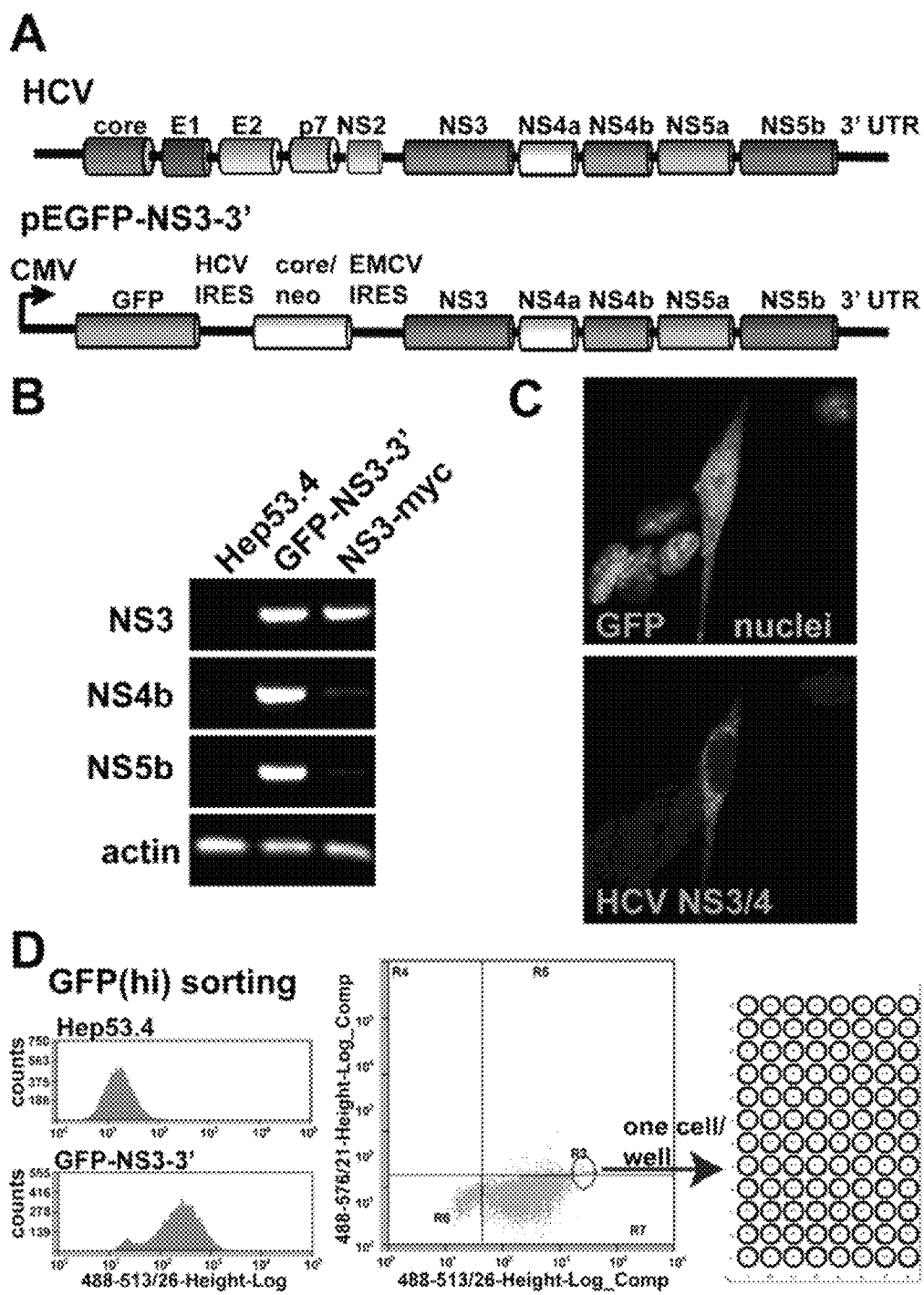
FIG. 1: Selection of stably-transfected mouse hepatoma cells producing HCV antigens from a sub-genomic HCV. A) Con1 NS3-3' replicon, containing most of the HCV non-structural coding region, was placed downstream of GFP in a modified pEGFP plasmid to produce GFP-NS3-3'; B) mRNA transcript coding for non-structural proteins NS3, NS4b and NS5b was detected in transient transfections of GFP-NS3-3' in Hep53.4 cells. The parental cell line, and Hep53.4 cells transfected with an NS3-myc expression plasmid were used as controls; C) Polyclonal anti-NS3/4 antibody specifically detected HCV proteins in GFP-NS3-3' transfected cells; D) Hep53.4 cells transfected with GFP-NS3-3' were selected with G418 for one month, then sorted based on GFP expression. Most cells displayed GFP signal above the parental cell line background signal (left-hand side). Cells with the strongest GFP signal were sorted one cell/well into a 96 well plate.

The present invention relates generally to modified hepatoma cell lines that express hepatitis C virus (HCV) antigens and which are capable of generating tumours in a syngeneic animal model. The cell lines are generated by genomic integration of an expression construct that comprises one or more HCV antigen-encoding sequences under the control of a constitutive promoter.

The cell lines are useful for testing prophylactic and therapeutic vaccines against HCV either in vitro or in vivo. Certain embodiments thus relate to in vitro methods of testing a candidate prophylactic or therapeutic HCV vaccine by contacting the hepatoma cell line according the invention with serum or immune cells isolated from an animal treated with the HCV vaccine. Certain embodiments relate to animal models comprising tumours derived from a hepatoma cell line according to the invention and in vivo methods of testing a candidate prophylactic or therapeutic HCV vaccine using these models.

In contrast to current cell lines and animal models developed for testing anti-HCV agents, the cell line disclosed herein does not require that the HCV sequences be capable of self-replication. Although HCV sequences that are capable of self-replication may be encompassed by some embodiments, this is not a necessary or required feature. Rather, the cell lines disclosed herein stably express the one or more HCV antigens from genomically integrated sequences under the control of a constitutive promoter. Accordingly, cells from the cell lines are capable of forming tumours in syngeneic immunocompetent animal models which maintain expression of the HCV proteins for a sufficient time to allow testing of candidate HCV vaccines.

Currently used recombinant HCV protein-expressing viruses poorly mimic a chronic viral infection, produce their own anti-viral response, and are not restricted to hepatocyte infection. Current HCV protein-expressing mouse tumour cells used for implantation into mice have not been of hepatocyte origin and have produced relatively small regions of HCV using simple expression systems, and thus poorly resemble HCV infected hepatocytes. Use of HCV+ve transgenic animals may be problematic in that the HCV proteins may be seen as "self" proteins, not foreign. The HCV-expressing tumour cells disclosed herein 1) are hepatocyte derived, 2) may be constructed to produce over half of the HCV protein content, and 3) are capable of producing HCV RNA transcript in cells that have a phenotype consistent with being infectable hepatocyte cells. Assessing vaccination against tumour growth in animals using these cells should mimic vaccinating against chronically infected hepatocytes to a good extent.

Definitions

Unless defined otherwise, all technical and scientific terms used herein have the same meaning as commonly understood by one of ordinary skill in the art to which this invention belongs.

The term "plurality" as used herein means more than one, for example, two or more, three or more, four or more, five or more, six or more, and the like.

The term "vaccine," as used herein, refers to a material capable of producing an immune response in a subject. A vaccine may be prophylactic in that it is administered to an individual who is free of the target disease or infection with the intention of reducing the risk that the disease or infection will occur, or it may be therapeutic in that it is administered to an individual suffering from the target disease or infection with the intention of treating the disease or infection.

As used herein, the term "treat" and grammatical variations thereof such as "treated" and "treating" when used with respect to a disease or an infection means to reduce, eliminate, ameliorate or stabilise the disease or infection, or one or more symptoms associated therewith.

The term "immune response," as used herein, refers to an alteration in the reactivity of the immune system of an animal in response to an antigen or antigenic material and may involve antibody production, induction of cell-mediated immunity, complement activation, development of immunological tolerance, or various combinations thereof.

As used herein, the term "about" refers to an approximately +/−10% variation from a given value. It is to be understood that such a variation is always included in any given value provided herein, whether or not it is specifically referred to.

The use of the word "a" or "an" when used herein in conjunction with the term "comprising" may mean "one," but it is also consistent with the meaning of "one or more," "at least one" and "one or more than one."

As used herein, the terms "comprising," "having," "including" and "containing," and grammatical variations thereof, are inclusive or open-ended and do not exclude additional, unrecited elements and/or method steps. The term "consisting essentially of" when used herein in connection with a composition, use or method, denotes that additional elements and/or method steps may be present, but that these additions do not materially affect the manner in which the recited composition, method or use functions. The term "consisting of" when used herein in connection with a composition, use or method, excludes the presence of additional elements and/or method steps. A composition, use or method described herein as comprising certain elements and/or steps may also, in certain embodiments consist essentially of those elements and/or steps, and in other embodiments consist of those elements and/or steps, whether or not these embodiments are specifically referred to.

It is contemplated that any embodiment discussed herein can be implemented with respect to any disclosed method or composition, and vice versa. Furthermore, the disclosed compositions and kits can be used to achieve methods of the invention.

Expression Constructs

Certain embodiments of the invention relate to expression constructs that may be integrated into the genome of mammalian hepatoma cell lines to produce a stable HCV antigen-expressing hepatoma cell line. The expression constructs comprise one or more HCV antigen encoding sequences under the control of a constitutive promoter. The expression construct further comprises nucleic acid sequences encoding a suitable selectable marker to allow for the screening and identification of successfully transfected cells. In certain embodiments, the expression construct may further comprise nucleic acid sequences encoding a reporter moiety to facilitate screening of transfected host cells for expression of the one or more HCV antigens.

In certain embodiments, the HCV antigen encoding sequences, the selectable marker encoding sequences and the reporter encoding sequences, when present, are all under the control of the constitutive promoter such that the sequences are transcribed on a single RNA molecule. In these embodiments, the expression construct may comprise one or more internal ribosome entry sites (IRES) to allow for translation of the different coding sequences.

Typically, in the expression construct, the sequences encoding the selectable marker and the sequences encoding the reporter, when present, are positioned upstream of the sequences encoding the one or more HCV antigens. Accordingly, in some embodiments, the expression construct comprises from 5' to 3': a constitutive promoter, a nucleic acid sequence encoding a selectable marker, and a nucleic acid sequence encoding a one or a plurality of HCV antigens. In some embodiments, the expression construct comprises from 5' to 3': a constitutive promoter, a nucleic acid sequence encoding a selectable marker, a nucleic acid sequence encoding a reporter, and a nucleic acid sequence encoding one or a plurality of HCV antigens. In some embodiments, the expression construct comprises from 5' to 3': a constitutive promoter, a nucleic acid sequence encoding a reporter, a nucleic acid sequence encoding a selectable marker, and a nucleic acid sequence encoding one or a plurality of HCV antigens. In certain embodiments in which the expression construct comprises sequences encoding a reporter which are transcribed on the same RNA transcript as the sequences encoding one or more HCV antigens, expression levels of the reporter should correlate to expression levels of the HCV antigen(s) and thus can facilitate screening and/or monitoring of HCV antigen expression.

The promoter comprised by the expression construct may be one of a variety of mammalian constitutive promoters known in the art. Examples include, but are not limited to, the simian virus 40 early promoter (SV40), cytomegalovirus immediate-early promoter (CMV), human Ubiquitin C promoter (UBC), human elongation factor 1α promoter (EF1A), mouse phosphoglycerate kinase 1 promoter (PGK), chicken β-actin promoter (CBA), chicken β-actin promoter coupled with CMV early enhancer (CAGG), human β-actin promoter (ACTB), mouse β-actin promoter (Actb), mouse albumin promoter (Alb), and functional variants of these promoters including, for example, chicken β-actin short promoter CBh and smCBA, and the like. Selection of an appropriate promoter for inclusion in the expression construct can be readily made by one skilled in the art.

The selectable marker encoded by the expression construct may also be one of a variety of known proteins that, when expressed in a cell, allow the cell to grow on a selective medium, thus allowing cells comprising the expression construct to be isolated from those that do not contain the expression construct. Typically, selectable markers are proteins that confer on the cells resistance to an antibiotic or that allow the cells to grow on a specific medium. Examples of suitable selectable marker encoding sequences include, but are not limited to, a neomycin (neo) resistance gene, puromycin (puro) resistance gene, dihydrofolate reductase (DHFR) gene (resistance to methotrexate), adenosine deaminase (ADA) gene, thymidine kinase (TK) gene, adenine phosphoribosyl transferase (APRT) gene, hygromycin resistance gene, and zeocin resistance gene. Selection of an appropriate selectable marker for inclusion in the expression construct can be readily made by one skilled in the art. In some embodiments, the expression construct comprises a neomycin resistance gene or a puromycin resistance gene.

The reporter encoded by the expression construct is typically a protein whose activity is easily detected in live cells, allowing cells expressing the reporter to be readily identified. Reporters include, for example, luciferase, luciferase variants, bioluminescent proteins and fluorescent proteins.

In certain embodiments, the reporter encoded by the expression construct is a fluorescent protein. The use of a fluorescent protein as a reporter permits rapid screening of cells expressing the protein using fluorescence activated cell sorting (FACS) and, if required, a rapid assessment of the relative level of expression in different cells. Examples of fluorescent proteins and their variants include, but are not limited to, green fluorescent proteins (such as, Emerald, EGFP, Azami Green, mWasabi, TagGFP, Kaede, ZsGreen, T-Sapphire and CopGFP), cyan fluorescent proteins (such as mCerulean, TagCFP, ECFP, AmCyan, Midoriishi Cyan and CyPet), blue fluorescent proteins (such as EBFP2, Azurite and mTagBFP), yellow fluorescent proteins (such as EYFP, Topaz, YPet, Venus, ZsYellow and mCitrine), orange fluorescent proteins (such as cOFP, Kusabira Orange, mOrange and mOrange2), red fluorescent proteins (such as Discosoma RFP (DsRed), monomeric red fluorescent protein 1 (mRFP1), mCherry, tdTomato, mStrawberry, mRuby, DsRed2, DsRed-T1, Anthomedusa J-Red and Anemonia AsRed2), far-red fluorescent proteins (such as Actinia AQ143, Entacmaea eqFP611, mPlum, mRasberry, Heteractis HcRed1, t-HcRed, TurboFP635, mKate and mNeptune), and near-infrared fluorescent proteins (such as and IFP1.4, eqFP650 and eqFP670). A large number of fluorescent proteins are commercially available from vendors such as Clonetech (Palo Alto, Calif.), Stratagene (La Jolla, Calif.), MBL International (Woburn, Mass.) and Evrogen JSC (Moscow, Russia).

The HCV antigen encoding sequence comprised by the expression construct encodes one or a plurality of HCV antigens. Typically the one or more HCV antigens will be one or more full-length proteins, however, antigenic fragments of HCV proteins are also contemplated in alternative embodiments.

As is known in the art, the HCV genome encodes at least 10 proteins including the structural proteins C (capsid), E1 and E2 (envelope glycoproteins) and p7, and the non-structural proteins, NS2, NS3, NS4A, NS4B, NS5A and NS5B. Accordingly, in certain embodiments, the HCV antigen encoding sequence comprised by the expression construct encodes between one and 10 HCV proteins or antigenic fragments thereof, for example between 2 and 10, between 3 and 10, between 4 and 10, between 5 and 10, between 6 and 10, between 7 and 10, between 8 and 10, or between 9 and 10 HCV proteins or antigenic fragments thereof, or any range therebetween, which may be selected from C, E1, E2, p7, NS2, NS3, NS4A, NS4B, NS5A and NS5B.

In some embodiments, the HCV antigen encoding sequences encode less than a full complement of HCV proteins, for example, between one and 9, between one and 8, between one and 7, between one and 6, or between one and 5, HCV proteins, or any range therebetween. In some embodiments, the HCV antigen encoding sequences encode a plurality of HCV proteins, for example, between 2 and 10, between 3 and 10, between 4 and 10, or between 5 and 10 HCV proteins, or any range therebetween.

In certain embodiments, the HCV antigen encoding sequence comprised by the expression construct encodes at least one protein selected from C, E1, E2, p7, NS2, NS3, NS4A, NS4B, NS5A and NS5B. In some embodiments, the HCV antigen encoding sequence comprised by the expression construct encodes a plurality of HCV proteins selected from C, E1, E2, p7, NS2, NS3, NS4A, NS4B, NS5A and NS5B. In some embodiments, the HCV antigen encoding sequence comprised by the expression construct encodes a plurality of HCV proteins which include at least NS2, NS3, NS4A, NS4B, NS5A and NS5B, and optionally one or more of C, E1, E2 and p7.

In some embodiments, the HCV antigen encoding sequence comprised by the expression construct encodes at least one non-structural protein selected from NS2, NS3, NS4A, NS4B, NS5A and NS5B. In some embodiments, the HCV antigen encoding sequence comprised by the expression construct encodes a plurality of HCV non-structural proteins selected from NS2, NS3, NS4A, NS4B, NS5A and NS5B. In some embodiments, the HCV antigen encoding sequence comprised by the expression construct encodes NS2, NS3, NS4A, NS4B, NS5A and NS5B.

In certain embodiments, the HCV antigen encoding sequence comprised by the expression construct may encode a plurality of HCV proteins that includes two or more copies of the same protein. For example, the HCV antigen encoding sequence may include two, three, four or more copies of a sequence encoding one HCV protein, or the HCV antigen encoding sequence may encode a plurality of different HCV proteins and may include one, two, three, four or more copies of each protein encoding sequence.

When the HCV antigen encoding sequences, the selectable marker encoding sequences and the reporter encoding sequences, when present, are all under the control of the constitutive promoter, the expression construct will typically comprise one or more IRESs to allow for translation of the different coding sequences. Various IRESs are known in the art and the skilled person can readily select an appropriate IRES for inclusion in the expression construct. Non-limiting examples include the natural HCV 5' IRES and the IRES from encephalomyocarditis virus (EMCV). In certain embodiments, the expression construct comprises HCV antigen encoding sequences, selectable marker encoding sequences and reporter encoding sequences under control of a single promoter and further comprises two IRESs to allow for efficient translation of all coding sequences.

The expression construct may optionally comprise one or more other regulatory or expression control sequences, such as terminators, enhancers and the like. In some embodiments, the expression construct may comprise sequences from the 5' UTR, the 3'UTR or both the 5' and the 3' UTR of the HCV genome that may assist with efficient translation or transcription of the HCV antigen encoding sequences. For example, the expression construct may comprise the IRES located at the 5' end of the HCV genomic RNA, the CRE element at the 3' end of the HCV genomic RNA, the 5BSL3 element, the stem-loop 5BSL3.2, or combinations thereof.

Vectors

Certain embodiments of the invention relate to vectors comprising the expression construct that facilitate transfection of the expression construct into the target host cell. The vector may be one of a variety of vectors known in the art that are capable of being transfected into mammalian cells, including various plasmids. A wide variety of suitable vectors are known in the art and may be employed as described or according to conventional procedures, including modifications, as described for example in *Current Protocols in Molecular Biology*, ed. Ausubel, F. M., et al., J. Wiley & Sons, Inc., New York, N.Y., and Sambrook J et al., 2000, *Molecular Cloning: A Laboratory Manual* (Third Edition), Cold Spring Harbor Laboratory Press, Long Island, N.Y.

In certain embodiments, the expression construct is cloned into a plasmid to facilitate transfection into the target cells. Various plasmids for transfection of mammalian cells are known in the art and commercially available. Selection of a suitable plasmid or other vector can be readily made by the skilled person.

The required sequences for the expression construct can be inserted into the vector by a variety of well-known procedures. In general, the DNA sequence is inserted into an appropriate restriction endonuclease site(s) by procedures known in the art. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described, for example, in Sambrook et al., ibid.; Ausubel et al., ibid., and elsewhere.

In some embodiments, the vector provides some of the sequences that make up the expression construct, for example, one or more of the promoter, reporter and other regulatory elements may be provided by the vector sequences and the other components of the expression construct are cloned into the vector in an appropriate orientation and position to generate the full-length expression construct within the vector. In these embodiments, the vector may be used to transfect the target host cell, or the expression construct may subsequently be excised or transcribed from the vector for further use, such as cloning into an alternative vector for transfection into the target host cell.

HCV-Expressing Hepatoma Cells

In certain embodiments, the invention relates to mammalian hepatoma cell lines that comprise an expression construct as disclosed above. Preferably, the hepatoma cell line comprises the expression construct stably integrated into the cell chromosome, however, hepatoma cell lines comprising a stably maintained plasmid comprising the expression construct and hepatoma cell lines transiently transfected with the expression construct are also encompassed in alternative embodiments.

The hepatoma cell line may be prepared, for example, by transfecting the cell line with a vector comprising the expression construct using standard techniques and selection protocols (see, for example, Sambrook et al., ibid.; Ausubel et al., ibid).

Recombinant clones may be screened by various standard methods to ensure that they express the HCV antigens encoded by the expression construct and, where appropriate, to ensure stable integration of the construct into the genome. For example, expression of the HCV antigens may be determined through immunochemical techniques using suitable anti-HCV antibodies and/or by detection of the RNA transcribed from the antigen-encoding sequences. Integration of the expression construct into the genome may be confirmed, for example, by PCR-based methods using genomic DNA extracted from the cells and appropriate primers. Other screening methods are well known to those of skill in the art.

When the expression construct includes a reporter gene, the transfected cell line may also be screened for expression of the reporter protein. When the reporter gene and the HCV antigen encoding sequences are under the control of a single promoter, reporter gene expression may be used as an indicator of HCV antigen expression. Recombinant clones that highly express the HCV antigens may thus optionally be identified by assessing the relative level of expression of the reporter protein in various clones by standard techniques. Appropriate screening techniques can be readily determined by one skilled in the art based on the nature of the reporter protein that is expressed by the construct. For example, fluorescent proteins can be detected by FACS analysis and luciferase can be detected using a luminometer in conjunction with appropriate reagents.

The cells may also be tested for albumin production by standard techniques to confirm the cells are of hepatocyte origin.

A number of different mammalian hepatoma cell lines are known in the art and may be suitable for transfection with the expression construct in various embodiments.

The hepatoma cell line may be selected for example based on the intended end use of the transfected cell line. For instance, if the hepatoma cell line is to be used to generate a tumour in an animal model, then a cell line that is compatible with this use will be selected. For example, a cell line that is syngeneic with the intended animal model, or sufficiently closely genetically related to avoid immune rejection of the cells. Suitable laboratory animals for generation of an animal model include, but are not limited to, rodents such as rats, mice and guinea pigs, rabbits, ferrets and non-human primates. Accordingly, in some embodiments, the hepatoma cell line will be a rodent, rabbit, ferret or non-human primate hepatoma cell line.

Examples of mammalian hepatoma cell lines include, but are not limited to, those available from the American Type Culture Collection (ATCC, Manassas, Va.) such as mouse hepatoma cell lines Hepa 1-6, Hepa 1c1c7, c37 (B7IFi1), c1 (B6NLxv1c2), c4 (B13NBii1), vT{2}, BpRc1, Tao BpRc1 and c12 (B15ECiii2) (all derived from C57L or C57L/J mice), and rat (*Rattus norvegicus*) hepatoma cell lines H-4-II-E, H4-II-E-C3 (from strain AxC), MH1C1, H4TG (from strain AxC), McA-RH7777 (from strain Buffalo), McA-RH8994, N1-51 (from strain Sprague-Dawley) and N1-51 Fudr (from strain Sprague-Dawley). Other examples include mouse hepatoma cell lines Hep53.4, Hep-55.1C, Hep-56.1B, Hep-56.1C and Hep-56.1D (from strain C57BL/6J); Hep-64.1 and Hep-66.3A (from strain B6C3F1), and HEP-70.4, Hep-74.3A, Hep-CLS-1W, Hep-CLS-C9 and Hep-CLS-E1 (from strain C3H/HE), available from CLS Cell Lines Service GmbH (Eppelheim, Germany).

In certain embodiments, the hepatoma cell line is a rodent hepatoma cell line. In some embodiments, the hepatoma cell line is a murine hepatoma cell line. In some embodiments, the hepatoma cell line is a non-human primate hepatoma cell line.

Animal Models

Certain embodiments of the invention relate to mammalian animal models suitable for testing prophylactic and therapeutic HCV vaccines. The animal models are generated by administering cells from a hepatoma cell line as described above to the animal and allowing the administered cells to form one or more tumours.

The animal will be selected based on the nature of the hepatoma cell line. For example the animal and the hepatoma cell line may be syngeneic, or genetically closely related. Suitable animals include but are not limited to, rodents such as rats, mice and guinea pigs, rabbits, ferrets and non-human primates.

Typically, an appropriate number of the stably transfected cells will be suspended in a suitable buffer or other carrier and injected or implanted in the animal. The number of cells injected or implanted in the animal will be dependent on the cell line used, the route of administration and the intended recipient, and can be readily determined by one skilled in the art. By way of example, in mice, a range of 100,000-10 million cells may be injected, depending on the injection route and the growth characteristics of the particular cell line.

The cells may be administered by a variety of routes, including for example, subcutaneous, intravenous or intraperitoneal injection or implantation. If desired, tumour establishment can be monitored, for example, by visual observation, palpation, caliper measurement, and the like. Expression of the HCV antigens by the tumour cells may be assessed by standard techniques such as those described above. In some embodiments, the cells are administered to the animal intraperitoneally.

At an appropriate time prior to or after administration of the hepatoma cells, the animal may be treated with the HCV vaccine and the effect of the vaccine on the growth of the tumour(s) can be monitored. A decrease in size of the tumour(s) and/or the number of the tumours after treatment is an indication of vaccine efficacy. Suitable time periods prior to or after administration of the hepatoma cells within which to administer the vaccine can be readily determined by those skilled in the art and would typically be between one or a few days and up to several weeks or months prior to or after administration of the hepatoma cells. Appropriate time period can readily be determined by the skilled worker based on the nature of the animal, the hepatoma cell line and the test vaccine. Exemplary, non-limiting time periods would comprise administering the test vaccine between about 1, 2, 3, 4 or 5 days and about 2 months, 6 weeks, 4 weeks, 3 weeks, 2 weeks or 10 days, or any time period therebetween, prior to or after administration of the hepatoma cells. Alternatively, in some embodiments, sufficient time to allow establishment of one or more tumours may be allowed to pass prior to administration of the test vaccine.

Methods & Uses

Various embodiments of the invention relate to method of using, and uses of, the expression constructs, cell lines and animal models disclosed herein.

The expression constructs may be used, for example, to generate a cell line that constitutively expresses one or more HCV antigens. Accordingly, certain embodiments relate to methods of producing a mammalian cell line that expresses one or a plurality of HCV antigens by transfecting the cell line with an expression construct as described above, and culturing the cell line under conditions that permit expression of the one or more HCV antigens. In some embodiments, the expression construct used in these methods may be comprised by a suitable vector. In certain embodiments, the cell line is a mammalian hepatoma cell line. In some embodiments, the cell line is a non-human mammalian hepatoma cell line.

Hepatoma cell lines that comprise the expression construct and are capable of constitutively expressing HCV antigens as described above may find use in in vitro methods for screening candidate prophylactic or therapeutic HCV vaccines. Accordingly, some embodiments of the invention relate to methods of testing an HCV vaccine in vitro. The method uses serum, or immune cells such as antibodies or T-cells, isolated from an animal that has been treated with the test vaccine. The immune cells may be isolated from the animal as a crude preparation, including as part of a blood or serum sample, or they may be purified or partially purified. The serum or immune cells are added to a culture of a hepatoma cell line as described above and the growth of the cell culture is monitored by standard techniques. A decrease in growth of the cell culture compared to an untreated control indicates that the serum or immune cells have an effect against the HCV antigens expressed by the cells, and that the vaccine is effective in stimulating an immune response against HCV. In some embodiments, the methods may further include positive controls, such as cells treated with known anti-HCV antibodies.

In some embodiments, the disclosed in vitro methods may be adapted for high-throughput, for example, through the use of multi-well plates and/or automated or semi-automated robotic systems, as is known in the art.

The hepatoma cell lines may also be used to generate an animal model for testing candidate prophylactic or therapeutic HCV vaccines in vivo. Accordingly, in some embodiments, the invention relates to methods of producing an animal model for testing prophylactic or therapeutic HCV vaccines that comprise administering to the animal cells from a hepatoma cell line as described herein that stably expresses one or more HCV antigens. The animal and cell line are selected such that they are syngeneic or genetically very closely related. This minimises the possibility of immune rejection of the administered cells and allows the use of fully immunocompetent animals. The cells may be administered to the animal by standard techniques, such as subcutaneous, intravenous or intraperitoneal injection or implantation. The HCV vaccine may be administered at an appropriate time point prior to or after administration of the hepatoma cells as described above. Alternatively, the animal may be monitored for the development of a tumour or tumours resulting from the growth of the administered cells and the vaccine administered once the tumour(s) reach an appropriate size or number. In some embodiments, the method may further comprise assaying cells from the tumour(s) for expression of the one or more HCV antigens.

The animal models described herein are thus useful for testing candidate prophylactic or therapeutic HCV vaccines in vivo. Accordingly, certain embodiments of the invention relate to methods of testing prophylactic or therapeutic HCV vaccines that comprise administering the HCV vaccine to an animal which bears one or more tumours formed from a hepatoma cell line as described above and assessing tumour growth in the animal. Assessing tumour growth may comprise monitoring changes in the size of a tumour or changes in the number of tumours over a period of time, or it may comprise assessing the size of a tumour or number of tumours present after a pre-determined time after administration of the vaccine has passed.

The animal may receive a single dose of the vaccine or one or more subsequent booster doses of the vaccine may be administered after the initial dose. Tumour growth may be assessed by standard techniques and compared to that in control animals. Suitable controls may include untreated animals, and optionally animals treated with a known HCV prophylactic or therapeutic and/or animals without tumours treated with the test vaccine. A decrease in tumour growth, which may include a decrease in the size of a tumour, a decrease in the number of tumours, or both, compared to an untreated control animal would be indicative that the test vaccine has an effect against HCV.

Typically, the effect of the test vaccine on tumour growth is assessed at least one to 3 weeks after administration of the vaccine to the animal, but shorter or longer time periods may be appropriate in some cases. Appropriate time periods can be readily determined by the skilled person. In certain embodiments, exemplary time periods within which to assess the effect of the test vaccine on tumour growth may be between about one week and two months. When tumour growth can be monitored non-invasively, then more than one assessment may be made within the selected time frame.

The cell lines and animal models described herein may also find use as research tools to investigate aspects of HCV infections. Certain embodiments of the invention thus relate to the use of the cell lines and animal models in basic research.

Kits

Certain embodiments of the invention relate to kits comprising the expression construct or transfected hepatoma cell lines described above.

Some embodiments relate to kits comprising an expression construct as described above for use to produce a HCV antigen expressing cell line. In some embodiments, the expression construct may be included in a suitable vector for transfecting the target cell line.

Some embodiments relate to kits comprising a mammalian hepatoma cell line stably transfected with an expression construct as described above that is capable of expressing the one or a plurality of HCV antigens encoded by the expression construct. The kit may optionally include one or more reagents required to maintain the cell line in culture, such as growth or maintenance media, salts, antibiotics, and the like.

In addition to the expression construct or cell line, the kits may optionally include reagents required to conduct assays or biological procedures, for example a transfection or reporter gene assay, such as buffers, salts, antibiotics, media, enzymes, enzyme co-factors, substrates, detection reagents, washing reagents, and the like. The kit may optionally include one or more control compounds.

In some embodiments, one or more of the components of the kit may be lyophilised and the kit may further comprise reagents suitable for the reconstitution of the lyophilised component(s).

The various components of each kit are provided in suitable containers. In some embodiments, the container may itself be a suitable vessel for carrying out a procedure or assay, for example, a microtitre plate, culture flask, or the like. Where appropriate, the kit may also optionally contain reaction vessels, mixing vessels and other components that facilitate the preparation of reagents or samples, or the carrying out of a procedure or assay.

In some embodiments, reagents comprised by the kit or their containers may be colour-coded to facilitate their use. When reagents are colour-coded, addition of one reagent to another in a particular step may for example result in a change in the colour of the mixture, thus providing an indication that the step was carried out.

The kit can optionally include instructions for use, which may be provided in paper form or in computer-readable form, such as a CD, DVD, USB device, or the like. The kit may also comprise computer readable media comprising software that assists in the interpretation of results obtained from using the kit.

To gain a better understanding of the invention described herein, the following examples are set forth. It will be understood that these examples are intended to describe illustrative embodiments of the invention and are not intended to limit the scope of the invention in any way.

EXAMPLES

Example 1

Generation of Expression Vector pEGFP-I389NeoNS3-3'

Methods

HCV sequence from the pFK-I389neo/NS3-3' replicon plasmid (obtained from Ralf Bartenschlager, University of Heidelberg, Germany) that encodes approximately 2/3 of the HCV transcript was excised and inserted into a modified pEGFP vector (Clonetech). This was performed by removing the HindIII-SpeI fragment of pFK-I389neo/NS3-3' and inserting this fragment into a circularized pCR2.1 plasmid (Invitrogen). A HindIII-XbaI fragment from this plasmid was then transferred into the pEGFP vector using the same restriction sites. Finally, a 5' HindIII fragment containing a G418 selection cassette from pFK-I389neo/NS3-3' was inserted into the pEGFP plasmid, with the correct orientation at the 5' end of the HCV-expressing cassette verified by restriction digest. The pEGFP that was used had been modified to replace the kanamycin/G418 selection cassette with an ampicillin selection cassette to enable subsequent selection of HCV-producing hepatoma cells in culture. Selection of cells was dependent on the G418 selection cassette present at the 5' end of the HCV encoding region (see FIG. 1). The resulting plasmid, pEGFP-I389NeoNS3-3' was used for hepatoma cell transfections.

Results

To generate hepatomas that would constitutively produce HCV antigens in vivo, the approach of using a genomically encoding sequence derived from an HCV replicon was adopted. Sequences from the pFK-1389neo-NS3-3' replicon were inserted downstream from a GFP expression cassette (FIG. 1A). Expression of GFP and HCV transcript and proteins produced by this plasmid were first verified in transient transfection assays of Hep53.4 cells (FIG. 1B, C). Transfected cells that expressed higher levels of GFP also displayed stronger HCV protein immunostaining.

Example 2

Generation and Testing of HCV-Antigen Expressing Hepatoma Cells

Methods

Generation of HCV-antigen Expressing Hepatoma Cells:

Appropriate expression of GFP and HCV proteins was first assessed with transient transfection of pEGFP-I389Neo-NS3-3' in a C57BL/6 hepatoma cell line, Hep53.4 (Cell Line Services, Germany). Subsequently, pEGFP-I389Neo-NS3-3' was used to generate stably-expressing cells derived from the Hep53.4 cell line. The initial selection of these cells was achieved with the addition of 2 mg/mL G418, maintained in culture for approximately one month. This concentration of G418 was found to kill 100% of untransfected Hep53.4 cells within five days. GFP expression was then used to screen for cells that may be producing higher levels of the HCV transcript, and HCV proteins.

To select cells that were strongly GFP+ve, fluorescence activated cell sorting (FACS) was used to isolate individual GFP+ve cells in 96-well tissue culture plate wells. Cells were put in suspension using Accutase (Millipore) and filtered through a 100 µm filter, then a 70 µm filter in a PBS+1% BSA solution added to the Accutase solution following several minutes of digestion. Using a MoFlo Astrios$^{EQ}$ high speed cell sorter (Beckman Coulter), GFP expressing cells were gated in two regions with the highest level of fluorescence (FITC channel, 488 nm excitation; 513/26 nm emission) (FIG. 1). Cells were collected in 50 mL DMEM+30% PCS+50 ug/mL gentamicin. After sorting, 100 uL of plain DMEM was added to each well to lower FCS to 10% and gentamicin to 16.6 µg/ml. Isolated cells that were strongly GFP+ve were expanded and frozen for storage or kept in culture for testing. Only cells that exhibited strong GFP expression and that resembled the parental cell line (Hep53.4 cells) were followed-up on.

Integration of an uninterrupted HCV coding sequence in GFP positive hepatoma clones was verified by PCR amplification of the NS3-5b coding region using genomic DNA isolated from the modified cells.

Detection of HCV RNA Expression:

Detection of NS3-5b RNA transcript expression in cell cultures of the recombinant clones was assessed. Total RNA was collected from cultured cells using an RNeasy mini kit (Qiagen). 500 ng RNA per sample was reverse-transcribed using M-MuLV reverse transcriptase (Invitrogen). Using the generated cDNA, the following primers corresponding to different regions of the HCV transcript were used to validate expression:

NS3 Primers:

```
                                         [SEQ ID NO: 1]
5'-CTACTCCCAACAGACGCGAGGCCTACTT-3'
and
                                         [SEQ ID NO: 2]
5'-CGCATAGTGGTTTCCATAGACTCGACGG-3'.
```

NS4b Primers:

```
                                         [SEQ ID NO: 3]
5'-GCCTCACACCTCCCTTACAT-3'
and
                                         [SEQ ID NO: 4]
5'-GCATGGCGTGGAGCAGTC-3'.
```

NS5b Primers:

```
                                         [SEQ ID NO: 5]
5'-TCTACGGGGCCTGTTACTCCATTGAGCC-3'
and
                                         [SEQ ID NO: 6]
5'-GGTCGGGCACGAGACAGGCTGTGATA-3'.
``` qPCR was performed using a standard Sybr Green detection protocol. Sybr Green master mix (Applied BioSystems) was mixed with cDNA reverse-transcribed from 500 ng RNA. Samples were amplified in a 7500 fast thermocycler. GAPDH and β-actin primers were used for normalization of HCV transcript sequences. Primer sequences were:

β-actin Primers:

```
                                         [SEQ ID NO: 7]
5'-CAGCCTTCCTTCTTGGGTAT-3'
and
                                         [SEQ ID NO: 8]
5'-TGGCATAGAGGTCTTTACGG-3'.
```

GAPDH Primers:

```
                                         [SEQ ID NO: 9]
5'-CTGGTCACCAGGGCTGCCATTTGCA-3'
and
                                         [SEQ ID NO: 10]
5' CACCGGCCTCACCCCATTTGATGT 3'.
```

Immunodetection of HCV and Albumin Protein Expression:

The expression of HCV proteins in recombinant hepatoma cells was performed by immunofluorescence detection using mouse monoclonal antibodies targeting the NS3

(clone 981) and (clone 388) NS5a proteins (Meridian Life Science, Inc.) and a goat polyclonal antibody generated against the HCV core+NS3+NS4 proteins (Virostat). An assessment of the production of albumin by the Hep53.4 and H12 cells was also performed by immunofluorescence using a rabbit polyclonal anti-albumin antibody (M140; Santa Cruz).

For detection by immunofluresence, 500,000 cells were seeded on either uncoated or collagen-coated coverslips in 6 or 12 well tissue culture plates, and left to expand and aggregate for two or five days, because aggregated cells were observed to better express albumin (a marker of hepatocyte differentiation). Cells were fixed in 4% paraformaldehyde, and stained using a standard immunofluorescence staining protocol utilizing Triton® X-100 permeabilization, described previously (Young et al., 2011). Secondary antibodies used included goat anti-rabbit AF488, donkey anti-mouse-AF546, and donkey anti-goat AF555 (Life Technologies) or donkey anti-rabbit cy5 (Jackson Immunoresearch). A 1 mg/mL solution of Hoechst dye was diluted 1:5000 in PBS, and used to label the cell nuclei. After final washing in PBS, the coverslips were mounted on microscope slides in fluorescence mounting medium and viewed on an Olympus FV1000 confocal microscope. Images were taken using a 40×, 1.4 NA objective lens with a 2× zoom. All images were exported as tiff files and processed with Adobe Photoshop and Illustrator for generating figures.

For immunoblotting, mammalian cell lysates from 6 well tissue culture plates were scraped into 200 μL of a 1× Laemmli buffer and boiled for five minutes, prior to chilling on ice and storing at −20° C. Secreted bacterial antigens were collected by adding 300 μL TCA to 1200 μL bacterial supernatant collected from small cultures grown overnight in LB medium. TCA-precipitated proteins were centrifuged at 4° C. for 10 min., and washed twice with ice-cold acetone. The resulting protein pellets were dried, and then resuspended in 1× Laemmli buffer. Protein lysates were run on standard 8-12% SDS-PAGE gels, and transferred into PVDF membranes for immunoblotting. Blotting was performed using a standard protocol with 5% milk in Tris-buffered saline for blocking. Monoclonal antibody used for HCV NS3 protein detection was as noted above. A rabbit polyclonal antibody directed against GFP (FL; Santa Cruz) and anti-actin mAb (JLA20; Developmental Studies Hybridoma Bank) were also used. Secreted bacterial fusion proteins were detected using an anti-YopE polyclonal antibody (bl-20; Santa Cruz) or an anti-HA epitope rabbit polyclonal antibody (Y-11; Santa Cruz). Appropriate HRP-labelled secondary antibodies were used (Santa Cruz) for detection of the primary antibodies, and ECL (Pierce) was used for chemiluminescence detection.

Results

Stably-transfected cell lines derived from pEGFP-I389Neo-NS3-3' transfected Hep53.4 cells were generated. Following selection using G418 and sorting based on GFP expression, several clones derived from single cells were isolated from 96 well plates. Only clones that continued to display strong GFP expression and which displayed a morphology similar to the parental Hep53.4 cell line were followed-up on. Of these, two clones, E3 and H12, displayed good growth and no loss of GFP expression. Prior to this, selection based only on the prolonged use of G418 selection inevitably led to a loss of GFP-expressing cells.

Figure 2:
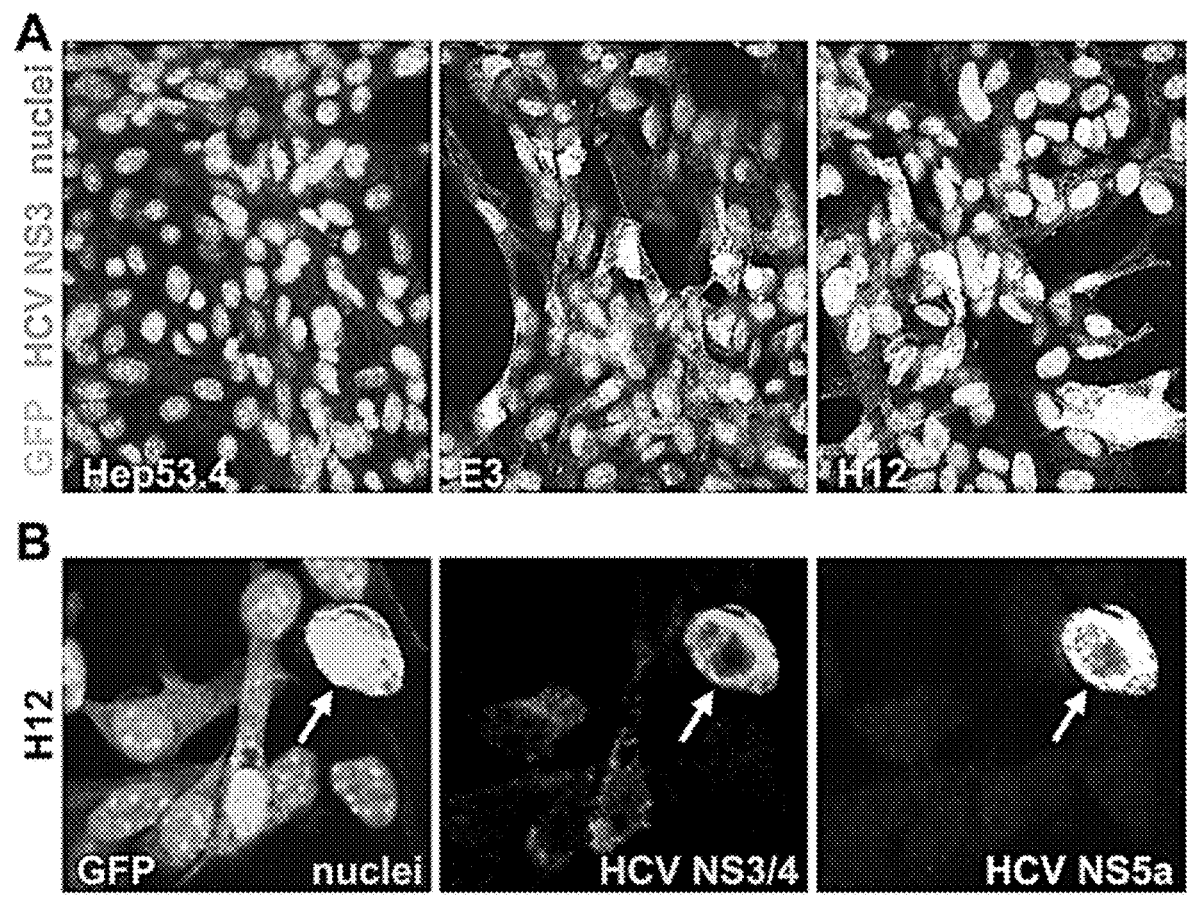
FIG. 2: Expression of HCV proteins in clonal recombinant cell lines. A) Immunofluoresence detection of NS3 protein in E3 and H12 cells using monoclonal antibody staining. The parental Hep53.4 cell line was used as a negative control. B) Immunostaining of HCV proteins in the H12 clone using an anti-core+NS3+NS4 polyclonal antibody and an anti-NS5a monoclonal antibody. The arrows in lower panels indicate a strongly GFP+ve cell clearly expressing multiple NS antigens.

E3 and H12 cells were analyzed for their expression of HCV antigens using three antibodies recognizing different HCV proteins. All recombinant cells expressed GFP detectable above the background signal of Hep53.4 parental cells. Both a polyclonal antibody generated against the HCV core+NS3+NS4 proteins, and a monoclonal antibody targeting NS3, detected protein in approximately 30% of the cells for both recombinant cell lines (FIG. 2). As noted in transient transfections (see Example 1), cells with an increased GFP signal also, in general, displayed stronger labeling with the anti-HCV antibodies. Using the H12 cell line, cells were labeled using the anti-HCV pAb (anti-core+NS3+NS4) and anti-NS5a mAb. Only a small number of cells (approximately 1%) were labeled with anti-NS5a antibody. All of these cells were also labeled clearly with the anti-HCV pAb. While some of the NS5a+ve cells also had very strong GFP signals, this was not always true, indicating that NS5a detection was not necessarily correlated with strong GFP and NS3/4 protein production. The localisation of all HCV staining in these cells was perinuclear, consistent with the endoplasmic reticulum localisation of HCV.

Clones E3 and H12 were assessed to ensure that all regions of the HCV transcript were being produced, and that the genomic integration of the construct did not disrupt the insert. Using RNA collected from H12 cells, RT-PCR amplification detected transcript corresponding to NS3, NS4 and NS5b. Amplification of the entire HCV open reading frame (ORF) using H12 genomic DNA produced a DNA band of the appropriate size. Using RNA collected from E3 cells, RT-PCR amplification detected appropriate transcripts corresponding to NS3 and NS5b, but not NS4. Correspondingly, HCV ORF could not be amplified from E3 genomic DNA. Therefore, the E3 clones contain an interrupted HCV ORF, whereas the H12 clone contains an intact HCV ORF capable of appropriate expression of NS3-NS5b proteins.

Immunoblotting indicated the production of appropriately-sized NS3 protein (predicted MW=67 kD) in the GFP-producing recombinant clones (FIG. 2B). To test the stability of HCV antigen expression in these cells without antibiotic selection, cells were cultured for up to 29 days with or without G418 (FIG. 2C). The expression of NS3 and GFP in these clones was maintained over this period.

Figure 3:
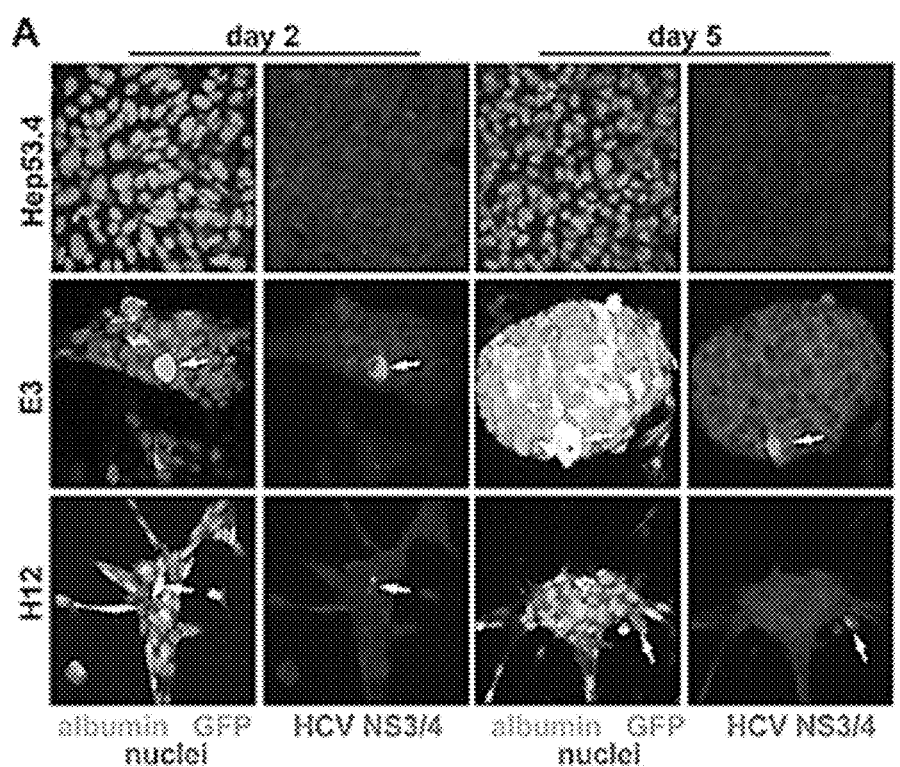
FIG. 3: Expression of HCV proteins and albumin in GFP(hi) hepatoma clones. Two clones, E3 and H12, were grown for two or five days in culture, following which the expression of HCV proteins and albumin was assessed. A polyclonal antibody against NS3/4 proteins showed staining in both, though this staining varied with only a few cells staining strongly (arrows). The cells formed clusters which displayed clear albumin staining. Albumin expression was increased with prolonged growth in vitro in both E3 and H12 clones. Albumin expression was not detectable in Hep53.4 parental cells in vitro.
Figure 4:
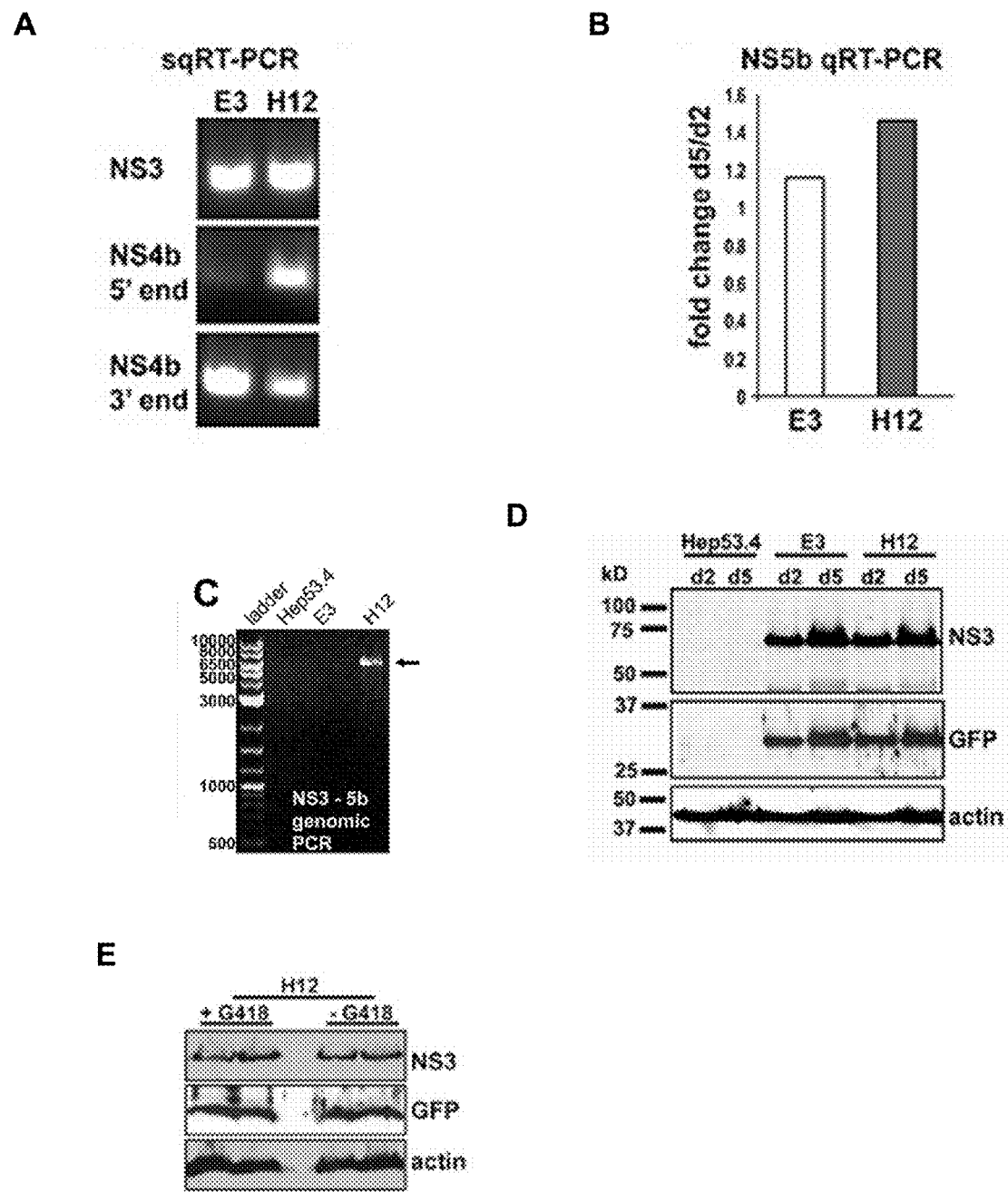
FIG. 4: A) RT-PCR showing expression of HCV transcript in the E3 and H12 clones. Primers were used to amplify sequence coding for a region of NS3 (primers: 5' CTACTC-CCAACAGACGCGAGGCCTACTT 3' [SEQ ID NO:1], and 5' CGCATAGTGGTTTCCATAGACTCGACGG 3' [SEQ ID NO:2], NS4b towards the 5' end (primers: 5' GAGTCCTAGCAGCTCTGGCCGCGTATT 3' [SEQ ID NO:15], and 5' ATGCCGGCGCCTACGAAAGCAGAAG 3' [SEQ ID NO:16]), and NS4b towards the 3' end (primers: 5' CTGTTGGCAGCATAGGCCTTGGGAAGGT 3' [SEQ ID NO:17], and 5' CTTGGACTGGAGCCAGGTCTT-GAAATCA 3' [SEQ ID NO:18]). H12 had intact expression of all HCV regions, and an intact HCV ORF in genomic DNA collected from the cells. The HCV ORF in E3 cells was interrupted in the NS4b coding region. B) NS5b transcript expression was increased >1.4 fold in the H12 clone from two to five days in culture, as assessed by qRT-PCR. C) PCR amplification of the NS3-5b open reading frame (ORF) off of genomic DNA collected from hepatoma cells. Only clone H12 had the entire ORF amplified (arrow). Primers used were 5' CTACTCCCAACAGACGCGAGGC-CTACTT 3' [SEQ ID NO:1]and 5' GGTCGGGCACGA-GACAGGCTGTGATA 3' [SEQ ID NO:6]. D) Detection of NS3 antigen in E3 and H12 cells by immunoblotting. Hep53.4 parental cell line lysates served as a negative control; detection of actin protein served as a loading control for all samples. E) Detection of stable NS3 antigen expression in H12 cells cultured without G418 antibiotic selection (−G418) for 29 days.

Albumin expression was examined in Hep53.4, E3 and H12 cells to examine whether these cells produced this characteristic hepatocyte protein (FIG. 3). Only mature, differentiated, hepatocytes normally produce albumin (Arteburn et al., 1995). Cells were allowed to grow for two or five days in culture after seeding a confluent monolayer for each cell line, with or without serum starvation to promote differentiation. Both E3 and H12 cells formed clusters after several days in culture. By five days in culture, albumin expression was clearly detected in these cells, indicating that these cell lines retain characteristics of mature hepatocytes (FIG. 3).

Example 3

Tumour Formation in C57BL/6 Mice Using H12 and Hep53.4 Cells

Methods

Clone H12 and the parental Hep53.4 cells were tested for their ability to form tumours in C57BL/6 mice. Tumour cells were implanted by intravenous, intraperitoneal, or subcutaneous injection routes. Intraperitoneal and subcutaneous injections consisted of 0.5-5 million H12 or Hep53.4 cells resuspended in PBS, in a total volume of 200 μL for intraperitoneal injection and 100 μL for subcutaneous injections. Subcutaneous injections were performed in the middle of the backs of the mice. Intravenous tail vein injections used 500,000 cells resuspended in 200 µL of PBS. Post-injection, animal health and weights were monitored daily. All work was performed in accordance with Canadian Council on Animal Care (CCAC) and local Animal Care Committee (ACC) guidelines.

Detection of HCV RNA Expression:

Detection of NS3-5b RNA transcript expression in tumours was assessed using a similar protocol to that described in Example 2. Total RNA was collected from liver or tumours using an RNeasy mini kit (Qiagen). The tissue was first immersed in RNAlater (Qiagen), and placed at 4° C. at least overnight. 500 ng RNA per sample was reverse-transcribed using M-MuLV reverse transcriptase (Invitrogen).

Using the generated cDNA, the primers described in Example 2, corresponding to different regions of the HCV transcript, were used to validate expression.

Immunodetection of HCV Protein Expression:

Immunodetection of HCV protein expression in tumours was performed using a similar protocol to that described in Example 2. Tumour sections were generated by snap-freezing unfixed tumours in Tissue-Tek OCT compound (Sakura Finetek), sectioned in a cryostat and mounted on Superfrost Plus slides (Fisher). Dried tissue sections were quickly rinsed with PBS and fixed for 10 min. with 4% paraformaldehyde. They were then washed three times in PBS, and stained using a protocol similar to that used for culture cells (Example 2). Anti-HCV goat polyclonal antibody, as above, was detected with donkey anti-goat-AF555 secondary antibodies (Life Technologies). Hoechst dye was used to label cell nuclei, as above. Confocal images were taken using a 20×, 0.75 NA or 40×, 1.3 NA objectives. All images were exported as tiff files and processed with Adobe Photoshop and Illustrator for generating figures.

Results

Figure 5:
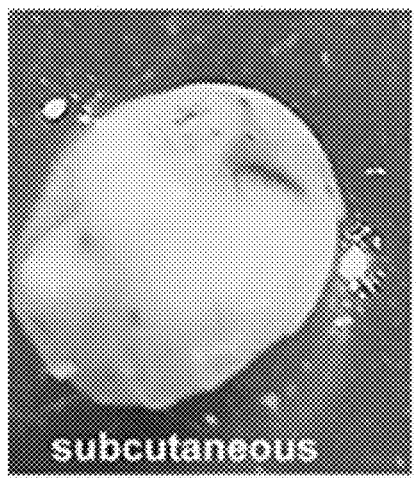
FIG. 5: Growth of HCV-recombinant tumours in mice. H12 tumours from A) subcutaneous at 14 d; B) the abdominal cavity at 21 d (intraperitoneal injections); C) the abdominal cavity at 28 d (intraperitoneal injections); D) the lungs at 28 d (intravenous injections). Arrows in C point to a liver-like lobe growing out of the tumour. Arrows in D point to tumour masses infiltrated into the lung parenchyma.
Figure 5:
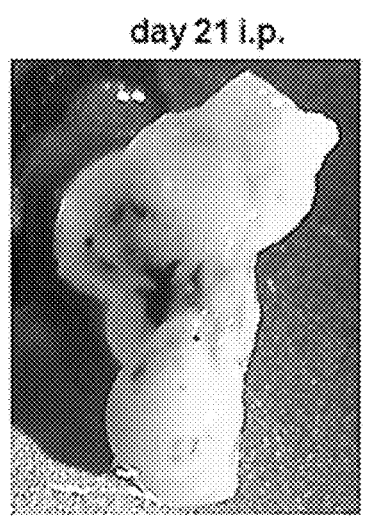
Figure 5:
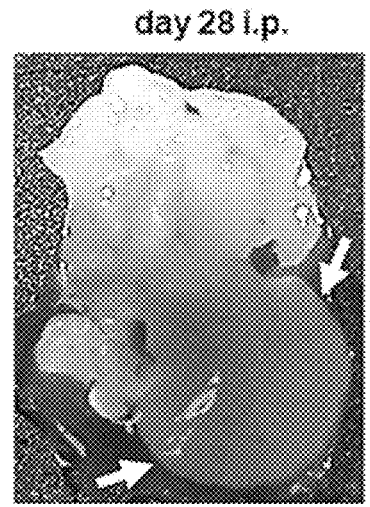
Figure 5:
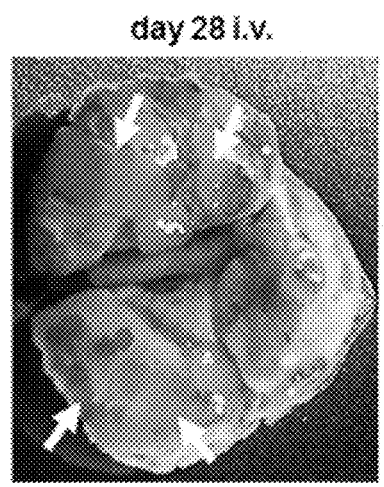

C57BL/6 mice were given subcutaneous, intravenous, or intraperitoneal injections of Hep53.4 and H12 cells to determine the tumourigenic potential of these cells. In all cases, tumour formation was observed for both cell lines with varying ability to maintain growth (FIGS. 5A-D and 6A-B). Subcutaneous tumours, while having the advantage of being easily monitored for growth, were prone to ulceration and shrank in size by two weeks post-implantation, which limited their usefulness in subsequent experiments. Intravenous injections resulted in tumour formation in the lungs (FIG. 5D). These tumours grew as visually obvious masses spread throughout the lung parenchyma.

Figure 6:
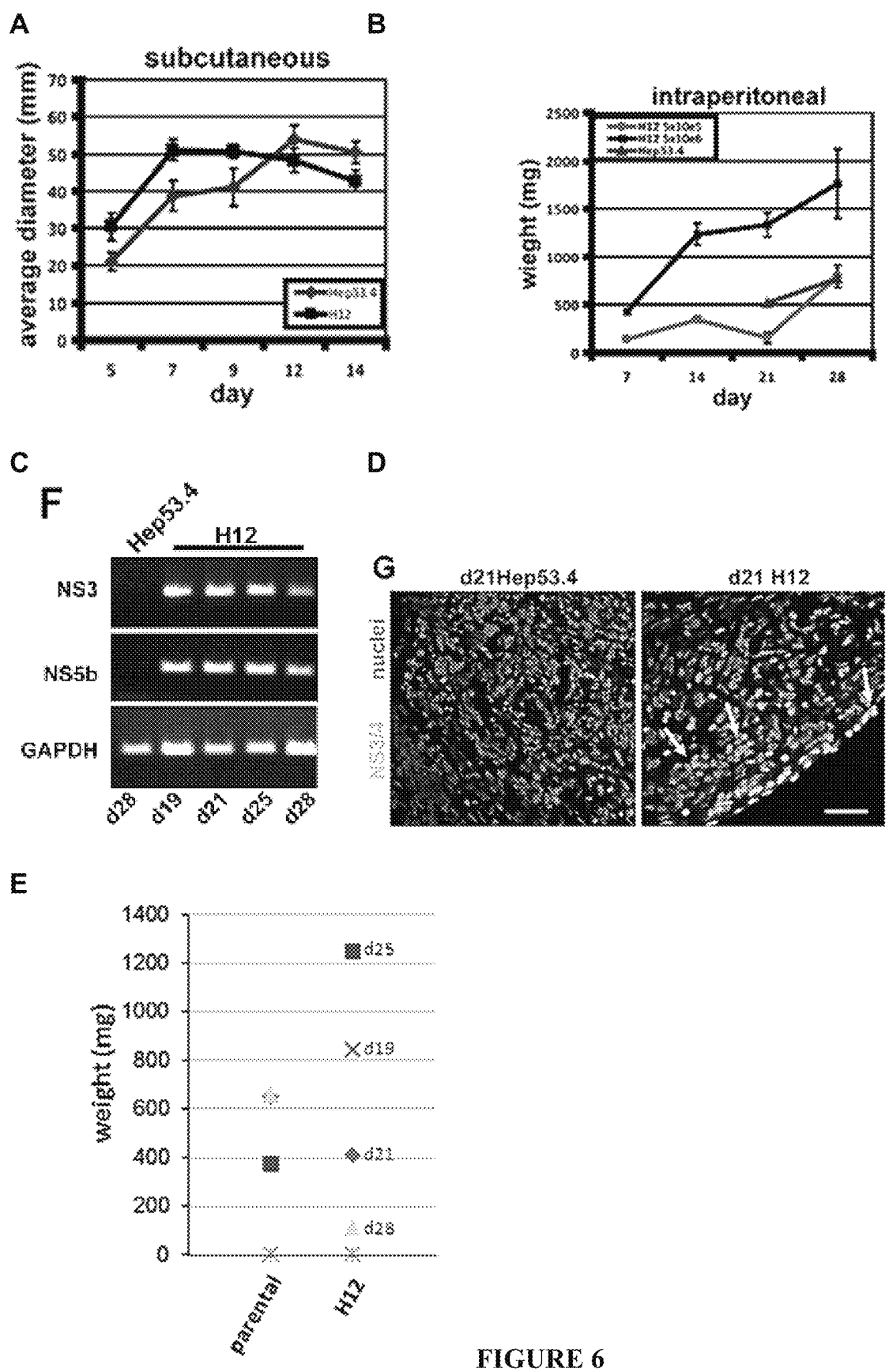
FIG. 6: Growth of HCV-recombinant tumours in mice. A) Growth curve of H12 and parental, Hep53.4, cells with subcutaneous implantations. Both cell types reached a maximum of around 50 mm before shrinking in size. These tumours were prone to ulceration between one and two weeks growth. B) Growth curve of H12 and Hep53.4 cells with intraperitoneal implantations. Both cell types continued to grow up to at least 28 d. C) HCV transcript expression from i.p. tumours, as shown using RT-PCR from total RNA collected from the tumours. A Hep53.4 tumour was used as a negative control. D) Immunofluorescence detection of NS antigens using a polyclonal anti-core+NS3+NS4 antibody in day 21 intraperitoneal tumours. HCV antigen-expressing cells are indicated with arrows. Scale bar=30 μm. E) Tumour weights at days 19-28 post-intraperitoneal injection of Hep53.4 or H12 cells. The Hep53.4 tumours were all collected at day 28.

Intraperitoneal injections generated discrete, hard tumour masses spread throughout the abdomen. These masses frequently grew near the stomach and liver, but were also found in every other part of the abdominal cavity. As these masses did not integrate into any organs, they could be dissected out and weighed to determine exact sizes (FIGS. 5C and 6B). In addition, these masses displayed the unique characteristic of developing soft liver lobe-like structures protruding from the main tumour mass (FIG. 5C). Intraperitoneal tumour cell injections were, therefore, chosen to be used for subsequent experiments involving vaccine testing.

Stable expression of the RNA encoding the NS3-5b HCV region was confirmed in intraperitoneal H12 tumours grown up to 28 days in the mice (FIG. 6C). There was no indication of a decrease in transcript expression over this time period. Histological examination of 21 day-old tumours using a goat polyclonal antibody against core+NS3+NS4 proteins indicated HCV antigen expression was maintained over this time period. Similar to expression in vitro, however, this expression was heterogeneous, with only a minority of cells having clear expression (FIG. 6D).

Example 4

Therapeutic HCV Vaccine Testing Using Intraperitoneal H12 Tumours

Candidate *Salmonella*-HCV Vaccine:

Recombinant attenuated *Salmonella typhimurium* was used to assess H12 tumour growth in response to a candidate therapeutic HCV vaccine. The attenuated AaroA SL1344 strain was used to generate recombinant attenuated *Salmonella typhimurium* that secrete HCV antigens via the type III secretion system. For this purpose, the SycE/YopE expression plasmid, pHR, was used (Rüssmann H, et al., 2000, *Eur J Immunol*. 30(5):1375-84; Tzelepis F, et al., 2012, *Cell Rep*. 2(6):1710-21).

A fusion protein coding region consisting of parts of the HCV NS3 and NS5a proteins was inserted in frame with the YopE. These sequences were chosen based on the location of epitopes targeted in human HCV infections (FIG. 8A) (Lechner et al., 2000). The regions used also contain an immunodominant epitope that is targeted in HLA A2.1 transgenic C57BL/6 mice (CINGVCWTV) (Fytili et al., 2008), and has been reported to be targeted in normal C57BL/6 mice (Krishnadas et al., 2010).

The NS3/5a fusion was generated by PCR amplification of DNA encoding NS3 (aa 45-231) and NS5 (aa 97-197) from HCV genotype 1b NS3 and NS5a encoding plasmids (pCMVTag1-NS3 and pCMVTag1-NS5a) (Addgene). The NS3 and NS5a regions were joined using a NotI linker, and inserted into a modified pHR plasmid (Rüssmann et al., 2000) using BamHI and XhoI sites. STΔaroA electroporated with the resulting plasmid were selected on ampicillin-containing (50 µg/mL) LB agar plates. Individual colonies were grown to an $OD_{600}$ of 0.7-1 in LB containing ampicillin (50 µg/mL) and aliquots were snap frozen in 15% glycerol. CFUs were determined using serial dilutions on LB agar plates. Secretion of the resulting YopE-NS3/5a protein was validated from in vitro supernatants using TCA precipitated proteins.

Figure 9:
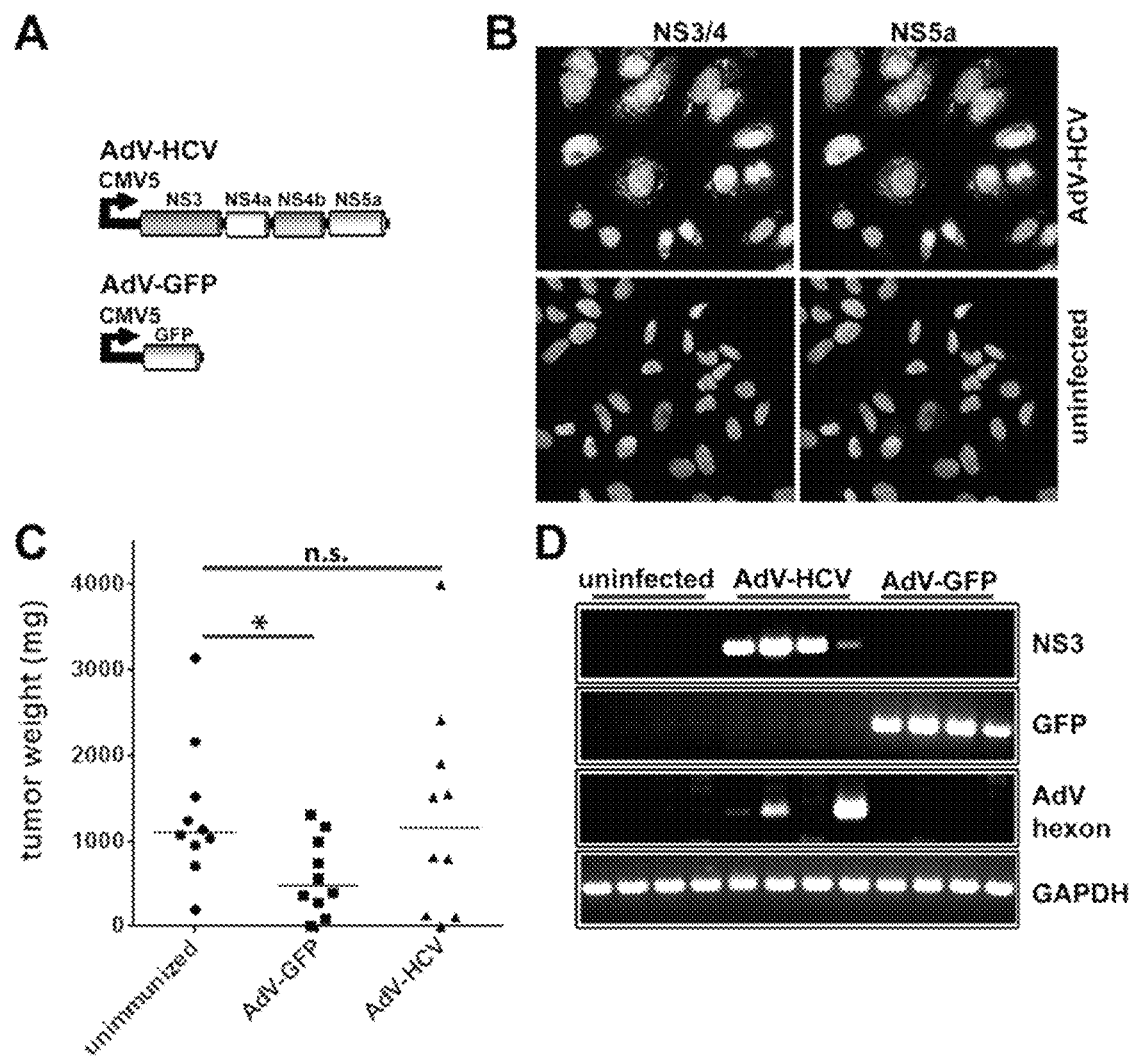
FIG. 9. Tumour growth following therapeutic vaccination with a recombinant adenovirus. A) Expression cassettes inserted into an Ad5 vector (AdV) used to express the HCV NS3-5a proteins, or GFP. B) Appropriate protein expression was confirmed for the HCV cassette using HeLa cell infections. C) Lack of efficacy of AdV-HCV in protecting against H12 cell tumour growth in a therapeutic testing model. Mice were implanted with H12 tumour cells and immunized as with the recombinant ST (FIG. 7). 1×10⁹ pfu adenovirus was injected intravenously. Mice injected with AdV-GFP had significantly smaller tumours compared to unimmunized mice (Mann-Whitney U test; *p<0.05). There was no difference between tumour sizes in the unimmunized animals and those immunized with AdV-HCV. D) Detection of HCV NS3 or GFP RNA in the mouse liver two weeks after intravenous infection with 1×10⁹ pfu of recombinant AdV. Transcript from the AdV hexon gene was also detected with AdV-HCV infections. GAPDH transcript detection served as a control for all samples.
Figure 10:
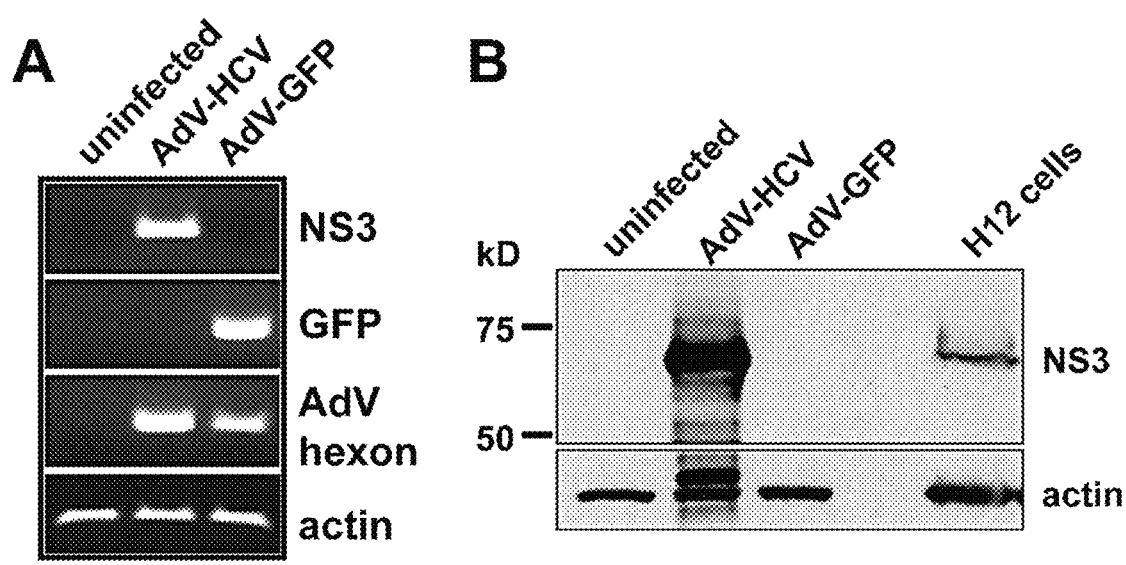
FIG. 10. HCV NS3 transcript and protein expression from AdV-HCV. A) RT-PCR from adenovirus infected (AdV-HCV or AdV-GFP) or uninfected HeLa cells demonstrated appropriate transcript expression. Primers used were: NS3, 5'GCGACCTGCGTCAATGGCGTGTGTT 3' [SEQ ID NO:19], and 5' TCGGCATGCCTCGTGACCAAGTAAA [SEQ ID NO:20]; GFP, 5' GAGAGGGTGAAGGTGATG-CAACATACGG 3' [SEQ ID NO:11], and 5' CAGCACGT-GTCTTGTAGTTGCCGTCATC 3' [SEQ ID NO:12]; hexon, 5' ATGGCTACCCCTTCGATGATGCCG 3' [SEQ ID NO:13], and 5' AGGGATGAACCGCAGCGT-CAAACGC 3' [SEQ ID NO:14]; actin, 5' CAGCCTTCCT- TCTTGGGTAT 3' [SEQ ID NO:7], and 5' TGGCATAGAG-GTCTTTACGG 3' B) Immunoblotting using protein lysates from infected HeLa cells with an anti-NS3 mAb detected protein of similar size to the NS3 protein produced by H12 hepatoma cells. An actin mAb was used to check loading.

Candidate Adenovirus-HCV Vaccine:

Recombinant adenovirus-HCV was used as a second candidate HCV vaccine to assess the responsiveness of the H12 therapeutic testing model. The recombinant replication-defective adenovirus serotype 5 (Ad5) encoding GFP regulated by the constitutive and strong CMV5 promoter has been described previously (Massie et al., 1998). Ad5 encoding the HCV antigen was made by homologous recombination in bacteria using the AdEasy plasmid system (He et al., 1998). The HCV sequence from the pFK-I389neo/NS3-3' replicon plasmid (obtained from Ralf Bartenschlager, University of Heidelberg, Germany) preceded by a CMV5 promoter (Massie et al., 1998) was inserted into the adenoviral shuttle vector used to generate the recombinant Ad plasmid (FIG. 10). A HindIII-BamHI restricted insert from the replicon plasmid containing the 5' translation initiation site and coding regions for the NS3, NS4a, NS4b and NS5a proteins was used. Ad-CMV5GFP and Ad5-CMV5-NS3-5a (Adv-HCV) (FIG. 9A) were amplified using SF-BMAd-R cells and purified by ultracentrifugation on CsCl gradients as described previously (Gilbert et al., 2014). Expression of the NS3-5a polypeptide was verified by immunoblotting and immunofluorescence staining of HeLa cells infected with the Ad5-CMV5-NS3-5a virus according to the protocol described in Example 2 (FIG. 9B and FIG. 10).

Methods

Initial use of H12 tumours for vaccine testing was performed using a therapeutic vaccination protocol. Tumours were first implanted intraperitoneally in the mice (see Example 3), followed by vaccination one week later. Recombinant STΔaroA or adenovirus were injected into the tail vein, in 200 μL of sterile saline (0.9% NaCl) (for STΔaroA) or a PBS buffer (for adenovirus).

For CD8$^+$ cell depletion, an anti-CD8$^+$ antibody was prepared (Young et al., 2012), with injections of 100 μg of antibody/mouse being performed on the same day as vaccinations, and again five days later.

Tumour sizes were measured following dissection two or three weeks post-vaccination. Tumours were then homogenized in DMEM, diluted in saline (0.9% NaCl), and plated on LB+streptomycin (50 μg/mL) plates to determine levels of the vaccine-strain *Salmonella* infection.

To determine the presence of the adenovirus infection, when adenovirus was used for the immunizations, RT-PCR was performed from liver-derived RNA at the end of the experiment. A protocol similar to that described in Example 2 was followed. Total RNA was collected from livers, the tissue was first immersed in RNAlater (Qiagen), and placed at 4° C. at least overnight. 500 ng RNA per sample was reverse-transcribed using M-MuLV reverse transcriptase (Invitrogen). Using the generated cDNA, the primers described in Example 2, corresponding to different regions of the HCV transcript, were used to validate expression. As well, detection of GFP and adenovirus hexon transcript using the following primers was used:

GFP Primers:

```
                                        [SEQ ID NO. 11]
5' GAGAGGGTGAAGGTGATGCAACATACGG 3'
and

[SEQ ID NO. 12]
5' CAGCACGTGTCTTGTAGTTGCCGTCATC 3'.
```

Hexon Primers:

```
                                        [SEQ ID NO. 13]
5' ATGGCTACCCCTTCGATGATGCCG 3'
and

[SEQ ID NO. 14]
5' AGGGATGAACCGCAGCGTCAAACGC 3'.
```

Clearance of the HCV+ve tumours was taken as an indication of vaccine efficacy.

Results

Candidate *Salmonella*-HCV Vaccine:

To test whether the recombinant H12 cells were susceptible to an anti-HCV immune response, a therapeutic vaccination assay protocol was used with intraperitoneal tumours. At two weeks post-vaccination, tumours were removed to assess sizes and the extent of vaccine-strain *Salmonella* infiltration (FIG. 7A). Attenuated *Salmonella* (STΔaroA), on its own, provided some inhibition of tumour growth (FIG. 7B). This is consistent with numerous studies demonstrating the tendency of *Salmonella* to infiltrate solid mass tumours and inhibit growth (Hiroshima et al., 2013; Frahm et al., 2015, reviewed in Hoffman and Zhao, 2014). Attenuated *Salmonella* that secreted truncated HCV NS3/NS5a (STΔaroA-HCV) antigens induced a greater inhibition of tumour growth compared to both unimmunized mice and mice immunized with STΔaroA (FIG. 7D).

The inhibition of tumour growth by STΔaroA-HCV was lost in mice co-injected with an anti-CD8 antibody which induces the depletion of CD8$^+$ cells. Mice immunized with STΔaroA-HCV and anti-CD8 antibody had tumours of similar sizes to those in the STΔaroA alone group. Mice injected with the CD8-depleting antibody alone had tumours of similar size to unvaccinated animals.

The reduced tumour size in STΔaroA-HCV immunized mice occurred despite reduced numbers of STΔaroA-HCV in vaccinated animals in spleen and tumour (FIG. 7C-E). The larger tumours exhibited lower than average numbers of bacteria (FIG. 7C). The smaller tumours in mice immunized with STΔaroA-HCV had widely varying numbers of bacteria, with several being lower than the numbers found in tumours from mice injected with STΔaroA alone. In general, the number of bacteria were found to be reduced in the STΔaroA-HCV vaccinated animals. This difference was significant in the infected spleens, though not in the tumours. This reduction in bacterial numbers is considered to be reflective of an immune response targeting the HCV antigen. Using a model antigen, OVA, it has previously been demonstrated the rapid decline in *Salmonella* numbers is due to a targeting of the infected cells by CD8$^+$ T cells (Tzelepis et al., 2012, ibid.).

Candidate Adenovirus-HCV Vaccine:

To test whether the recombinant H12 cells were susceptible to an anti-AdV-HCV immune response, a therapeutic vaccination assay protocol similar to that used with the STΔaroA-HCV was followed. Immunization with AdV-HCV was compared to AdV-GFP, which would also have the potential to control tumour growth, as the H12 cells also express GFP antigen.

Using the therapeutic vaccination protocol used for assessing STΔaroA-HCV, AdV-HCV failed to demonstrate any benefit in limiting H12 tumour growth. Injection of AdV-GFP at one week post-tumour cell implantation did reduce tumour growth compared to unimmunized animals (FIG. 9C). However, the median tumour size was not reduced compared to unimmunized mice when using AdV-HCV. Mice immunized with either AdV-HCV or AdV-GFP displayed clear expression of their respective antigen transcript in the livers at two weeks post-vaccination (FIG. 9D). The AdV-HCV immunized mice also retained detectable levels of adenovirus transcript (AdV hexon transcript). No antigen or adenovirus-related transcript expression was detected in the H12 tumours at the same time point post-immunization (data not shown).

Example 5

Generation of Protective Antigen-Specific Response by NS3/5a Recombinant Bacteria A *Listeria* (Lm) challenge model was used to confirm the identification of STΔaroA-HCV, by the antigen-expressing hepatoma tumour model described herein, as able to generate a protective antigen-specific response. Rapid protection against a secondary Lm infection is mediated primarily by a CD8$^+$ T cell response (Kagi et al., 1994, Harty and Bevan, 1995, White and Harty, 1998). Accordingly, recombinant Lm that produces and secretes HCV antigens similar to those produced in the recombinant STΔaroA (FIG. 8A) was generated.

Methods

Recombinant *Listeria monocytogenes* (Lm) was generated to secrete a fusion protein encoding NS3 aa 176-231 and NS5a aa 97-197 from the same HCV template DNA as used for the recombinant *Salmonella* vaccine (Example 4). The relevant HCV sequence was PCR-amplified from the pHR-NS3/5a plasmid and inserted into pJJD, a shuttle vector used for homologous recombination in Lm (Shen et al., 1995). An LLO-NS3/5a fusion protein that can be secreted from the Lm was generated. Roughly half of the NS3 N-terminal sequence was removed to enable its production, as the longer NS3/5a fusion sequence in the STΔaroA could not be produced by the Lm. A control construct, producing an LLO-LCMV nucleoprotein fusion protein (LLO-NP) was generated in a similar manner, using sequence encoding LCMV NP aa 287-461. LCMV template came from recombinant *Salmonella* that had been previously generated to secrete the LCMV NP antigen (Tzelepis et al., 2012).

Following cloning into the pJJD vector in *E. coli*, the expression plasmids were electroporated into Lm, and colonies were selected on BHI agar plates with X-gal and erythromycin (5 µg/mL) (Shen et al., 1995). The resulting Lm-NS3/5a and Lm-NP recombinant bacteria were grown in BHI broth with erythromycin to an $OD_{600}$ of 0.7-1, aliquoted, and frozen in 15% glycerol at −80° C. CFUs were determined by serial dilution and plating on BHI agar plates. Secretion was verified by immunoblotting TCA-precipitated proteins from the culture supernatant, as described above for the *Salmonella*-secreted antigen. An antibody directed against an internal HA tag (Y11; Santa Cruz) was used to detect the fusion proteins.

Mice were immunized with intravenous injections of recombinant STΔaroA secreting either an LCMV antigen, NP, or an NS3/5a fusion antigen. Thirty days later, the mice were challenged with recombinant Lm secreting either the LCMV or the HCV antigen. Mice were injected with both recombinant STΔaroA and Lm in the tail vein, with bacteria resuspended in sterile saline. Three days post Lm challenge, mice were euthanized and the Lm infection was quantified. Spleens were homogenized, serially diluted in sterile saline, and plated on BHI agar plates with erythromycin.

Results

Figure 7:
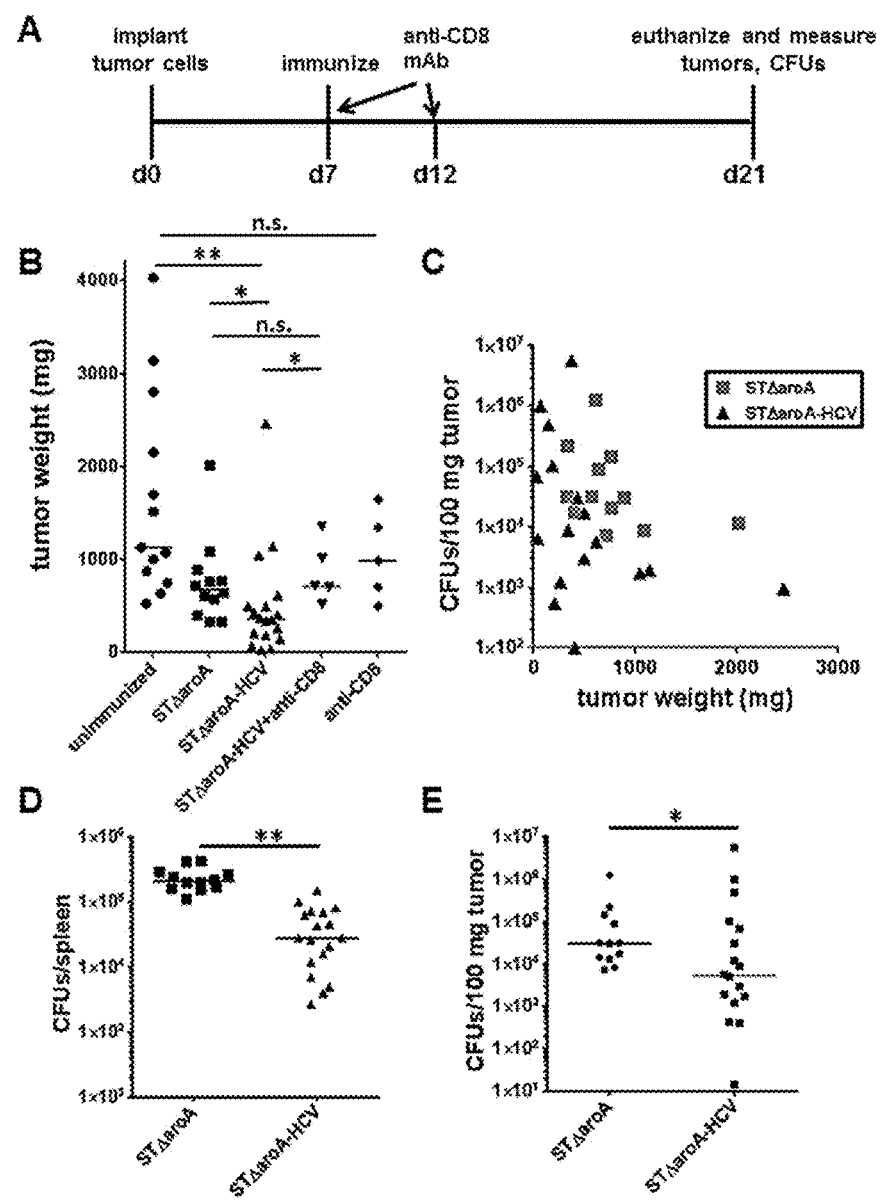
FIG. 7: Tumour growth following therapeutic vaccination with candidate recombinant *Salmonella*. A) Mice were immunized using a therapeutic protocol, one week post-H12 tumour cell implantation, with 1×10⁵ attenuated *Salmonella*. Intraperitoneal injections of 4×10⁶ H12 cells were used. Tumour sizes and bacterial CFUs were assessed at two weeks post-vaccination. B) Mice immunized with STΔaroA-HCV had significantly smaller tumours compared to unimmunized and mice, and mice immunized with the parental bacterial strain (STΔaroA) (Mann-Whitney U test; *p<0.05, **p<0.005). Medians are indicated with bars. In STΔaroA-HCV immunized mice treated anti-CD8 depleting antibody, tumour sizes were most similar to mice immunized with STΔaroA control bacteria. Tumour sizes from mice treated with anti-CD8 antibody alone were most similar to those from the unvaccinated and untreated group. C) Tumour sizes did not correlate well with bacterial numbers in mice immunized with STΔaroA-HCV. Bacterial CFUs in the tumours themselves ranged by several orders of magnitude in similarly-sized tumours. The very largest tumours from STΔaroA-HCV and STΔaroA immunized mice did have low CFU numbers (~1×10⁴ or lower), reflective of the bacteria having some direct influence on tumour size. However, several of the STΔaroA-HCV immunized mice with small tumours also had well under 1×10⁴ CFUs. D, E) Spleen (D) and tumour (E) CFUs from mice immunized with STΔaroA or STΔaroA-HCV.

The antigen-expressing hepatoma tumour model described herein identified the ability of STΔaroA and STΔaroA-HCV immunization to generate a protective antigen-specific response. Specifically, STΔaroA immunizations alone were shown to reduce HCV antigen-expressing tumour size, reflective of the intrinsic anti-tumour activity of *Salmonella* (FIG. 7B). Immunization with STΔaroA-HCV, secreting a fusion protein of HCV non-structural protein regions, exhibited further reduced tumour sizes. Importantly, this was independent of bacterial numbers, and dependent on the presence of $CD8^+$ immune cells (FIG. 7).

Figure 8:
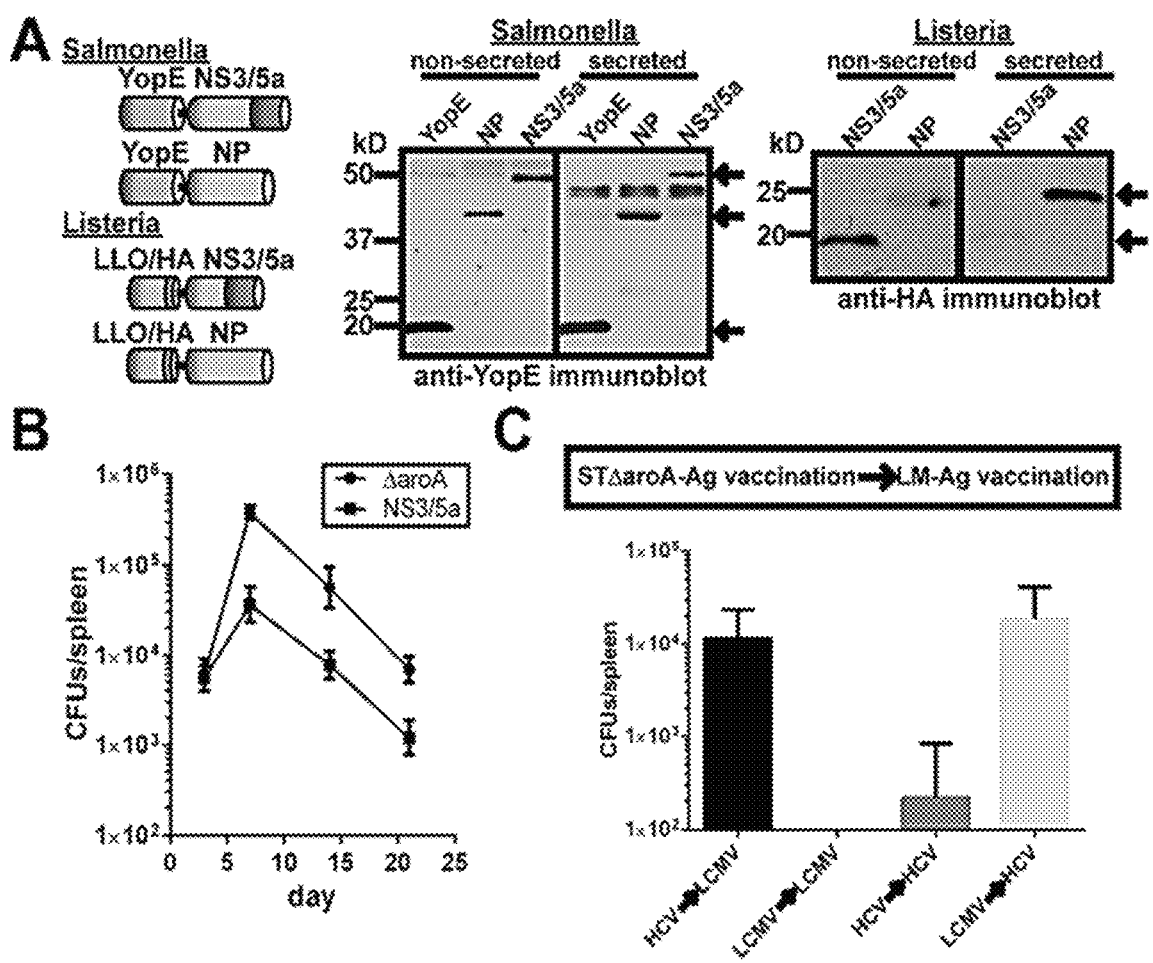
FIG. 8. Recombinant HCV antigen-secreting *Salmonella* protect against a recombinant *Listeria* challenge. A) Fusion proteins produced in recombinant *Salmonella* (STΔaroA) and *Listeria* (Lm). YopE mediated HCV (NS3/5a) or LCMV (nucleoprotein; NP) antigen secretion from STΔaroA. Lysteriolysin (LLO) mediated secretion from *Listeria*. The HCV NS3 antigen region was truncated in Lm to enable production and secretion of the fusion protein. An HA epitope allowed for antibody detection of the Lm fusion proteins. Fusion protein production and secretion was validated by immunoblotting bacterial lysates and culture supernatants. YopE fusion proteins were well detected in pellet (non-secreted) and supernatant (secreted) samples from recombinant *Salmonella* cultures. With recombinant *Listeria*, the Lm LCMV NP antigen was comparatively better secreted, though secreted NS3/5a was detected from Lm supernatant (arrows). B) Growth of recombinant STΔaroA producing the NS3/5a fusion protein, in infected C57BL/6 mice. CFUs from 4 mice/group/time point was collected. C) Protection against a recombinant *Listeria* challenge by prior immunization with recombinant STΔaroA. C57BL/6 mice were immunized with 1×10⁵ STΔaroA-HCV or STΔaroA-LCMV then challenged 30 d later with 1×10⁴ Lm-HCV or Lm-LCMV. At day 3 following the Lm challenge, mice were sacrificed and Lm CFUs were quantified from spleens. The numbers are from three separate experiments, with 3 or 4 mice/group/experiment.

The identification of the candidate *Salmonella*-vectored vaccine as able to produce a protective response against HCV antigens was further confirmed using recombinant Lm in a heterologous challenge assay wherein protection against an infection of Lm secreting a similar HCV antigen region as that used in the STΔaroA-HCV was further demonstrated (FIG. 8).

Mice immunized with the LCMV antigen-secreting *Salmonella* had completely cleared the Lm-LCMV, but not Lm-HCV secreting the irrelevant antigen. Mice immunized with the HCV antigen-secreting *Salmonella* had a greatly diminished number of Lm-HCV, but relatively high numbers of Lm-LCMV, indicating the production of a protective response specific to the HCV antigen.

Example 6

Generation of Replicon Plasmid pFK-I389puro

A replicon plasmid, pFK-I389puro, wherein the majority of the HCV coding region was replaced with a puromycin resistance enzyme (Pac) coding region was generated in order to confer resistance to cells capable of replicating the Pac transcript. Replication is presumably dependent on the transfected cells co-expressing the HCV NS5b RNA polymerase at sufficient levels, along with other proteins of the HCV replication complex (NS3, NS4a, NS4b, NS5a).

pFK-I389puro was generated by inserting a Pac gene flanked by AscI and SpeI restriction sites into the pFK-I389neo/NS3-3' plasmid. The HCV 5BSL3 region (You S, et al., 2004, *J Virol.* 78(3):1352-66) and 3' UTR was then added into the SpeI site of the plasmid using a PCR amplified 3' end with SpeI sites added at each side. Orientation of the 3' end was confirmed by restriction digest. This construct was linearized with ScaI and purified for use in an in vitro transcription reaction using T7 polymerase. The RNA generated from this transcription was transfected into H12 cells, and cells were subsequently selected with puromycin (2 µg/mL).

The survival of H12 tumour cells carrying the I389puro RNA using puromycin selection is dependent on the cells producing a fully functional HCV replication complex. This approach ensures that the cells not only produce an HCV polypeptide encoding NS3, NS4a, NS4b, NS5a, and NS5b, but also that these proteins are cleaved from the immature polypeptide and are functional in the cells. It is predicted that this approach will more closely mimic the situation in HCV-infected hepatocytes.

The disclosures of all patents, patent applications, publications and database entries referenced in this specification are hereby specifically incorporated by reference in their entirety to the same extent as if each such individual patent, patent application, publication and database entry were specifically and individually indicated to be incorporated by reference.

Although the invention has been described with reference to certain specific embodiments, various modifications thereof will be apparent to those skilled in the art without departing from the spirit and scope of the invention. All such modifications as would be apparent to one skilled in the art are intended to be included within the scope of the following claims.

We claim:

1. A hepatitis C virus (HCV)-antigen expressing, non-human mammalian hepatoma cell comprising an expression construct stably integrated into the genome of the cell, the expression construct comprising a promoter sequence operably linked to:
   a first nucleic acid sequence encoding a plurality of hepatitis C virus (HCV) non-structural proteins selected from NS3, NS4a, NS4b, NS5a and NS5b, and
   a second nucleic acid sequence encoding a selectable marker,
   wherein the cell constitutively expresses the plurality of HCV non-structural proteins without HCV replication.

2. The cell according to claim 1, wherein the expression construct comprises a third nucleic acid sequence encoding a reporter.

3. The cell according to claim 1, wherein the second nucleic acid sequence is upstream of the first nucleic acid sequence and the second and first nucleic acid sequences are transcribed as a single RNA molecule.

4. The cell according to claim 3, wherein the expression construct further comprises an internal ribosome entry site upstream of the first nucleic acid sequence.

5. The cell according to claim 2, wherein the third nucleic acid sequence is upstream of the first and second nucleic acid sequences and the third, second and first nucleic acid sequences are transcribed as a single RNA molecule.

6. The cell according to claim 5, wherein the expression construct further comprises a first internal ribosome entry site (IRES) upstream of the second nucleic acid sequence and a second IRES upstream of the first nucleic acid sequence.

7. The cell according to claim 1, wherein the first nucleic acid sequence further encodes one or more HCV structural proteins.

8. The cell according to claim 1, wherein the cell is a murine hepatoma cell.

9. The cell according to claim 1, wherein the cell is capable of forming a tumour when administered to a syngeneic mammal.

10. A method of producing a non-human mammal suitable for testing prophylactic and therapeutic hepatitis C virus vaccines to stimulate an immune response against HCV, the method comprising administering the cell according to claim 1 to a immunocompetent animal, and allowing the cell to proliferate and form a tumour in the animal, wherein the cell and the immunocompetent animal are syngeneic.

11. The method according to claim 10, wherein the cell is administered to the animal by intravenous, intraperitoneal or subcutaneous injection.

12. A kit comprising the cell according to claim 1 and instructions for use.

* * * * *